(12) United States Patent
Kikuchi et al.

(10) Patent No.: US 11,807,679 B2
(45) Date of Patent: Nov. 7, 2023

(54) ANTI-CKAP4 MONOCLONAL ANTIBODY

(71) Applicant: OSAKA UNIVERSITY, Suita (JP)

(72) Inventors: Akira Kikuchi, Suita (JP); Katsumi Fumoto, Suita (JP); Hirokazu Kimura, Suita (JP)

(73) Assignee: OSAKA UNIVERSITY, Suita (JP)

( * ) Notice: Subject to any disclaimer, the term of this patent is extended or adjusted under 35 U.S.C. 154(b) by 688 days.

(21) Appl. No.: 16/650,337

(22) PCT Filed: Sep. 26, 2018

(86) PCT No.: PCT/JP2018/035719
§ 371 (c)(1),
(2) Date: Mar. 24, 2020

(87) PCT Pub. No.: WO2019/065747
PCT Pub. Date: Apr. 4, 2019

(65) Prior Publication Data
US 2020/0377580 A1    Dec. 3, 2020

(30) Foreign Application Priority Data

Sep. 26, 2017    (JP) .................................. 2017-185090

(51) Int. Cl.
| | |
|---|---|
| *C07K 16/18* | (2006.01) |
| *A61P 35/00* | (2006.01) |
| *G01N 33/543* | (2006.01) |
| *G01N 33/574* | (2006.01) |
| *A61K 39/00* | (2006.01) |

(52) U.S. Cl.
CPC .............. *C07K 16/18* (2013.01); *A61P 35/00* (2018.01); *G01N 33/543* (2013.01); *G01N 33/57423* (2013.01); *G01N 33/57438* (2013.01); *A61K 39/00* (2013.01); *C07K 2317/24* (2013.01); *C07K 2317/33* (2013.01); *C07K 2317/73* (2013.01); *C07K 2317/76* (2013.01)

(58) Field of Classification Search
CPC ....... G01N 33/57423; G01N 33/57438; G01N 33/543; G01N 2800/52; G01N 33/57446; C07K 16/18; C07K 2317/24; C07K 2317/33; C07K 2317/73; C07K 2317/76; C07K 2317/34; C07K 14/71; C07K 16/28; A61P 35/00; A61P 37/04; A61K 39/00; A61K 2039/505; A61K 39/395
See application file for complete search history.

(56) References Cited

U.S. PATENT DOCUMENTS

2018/0037649 A1* 2/2018 Kikuchi et al. .......... C12Q 1/68

FOREIGN PATENT DOCUMENTS

| EP | 3 206 032 A1 | 8/2017 |
| WO | 2016/136372 A1 | 9/2016 |

OTHER PUBLICATIONS

Chavda et al., Antiproliferative factor (APF) binds specifically to sites within the cytoskeleton associated protein 4 (CKAP4) extracellular domain, BMC, 2017, 18:13.*
Tzartos et al, Epitope Mapping by Antibody Competition, Springer, 1996, p. 55-66.*
Edwards et al, The Remarkable Flexibility of the Human Antibody Repertoire; Isolation of Over One Thousand Different Antibodies to a Single Protein, BLyS, 2003, 103-118.*
2018, Almagro et al., Humanization of Antibodies, Frontiers in Bioscience, 2008, 1619-1633.*
Gershoni et al., Epitope Mapping, Biodrugs 2007; 21 (3): 145-156.*
Blythe et al., Benchmarking B cell epitope prediction: Underperformance of existing methods, Protein Science (2005), 14:246-248.*
Schreiber et al.,3D-Epitope-Explorer (3DEX): Localization of Conformational Epitopes within Three-Dimensional Structures of Proteins, Wiley Interscience, 42-44, 60596.*
Lumen Learning https://courses.lumenlearning.com/suny-microbiology/chapter/polyclonal-and-monoclonal-antibody-production/ Oct. 2, 2016 (Year: 2016).*
Kimura H et al. CKAP4, a DKK1 Receptor, Is a Biomarker in Exosomes Derived from Pancreatic Cancer and a Molecular Target for Therapy. Clin Cancer Res (2019) 25 (6): 1936-1947 (Year: 2019).*

(Continued)

*Primary Examiner* — Adam Weidner
*Assistant Examiner* — John J Skoko, III
(74) *Attorney, Agent, or Firm* — Knobbe Martens Olson & Bear LLP

(57) ABSTRACT

The purpose of the present invention is to provide an anti-CKAP4 monoclonal antibody that inhibits the binding of DKK1 and CKAP4 and exhibits an exceptional antitumor effect. Provided is an anti-CKAP4 monoclonal antibody that recognizes at least part of the 451-455 region, at least part of the 481-485 region, at least part of the 502-510 region, at least part of the 503-524 region and at least part of the 585-590 region, or at least part of the 585-592 region of the amino acid sequence (amino acid sequence of CKAP4) represented by SEQ ID NO:1 as an epitope, the anti-CKAP4 monoclonal antibody effectively inhibiting the binding of DKK1 and CKAP4, the activation of AKT of S2-CP8 cells, and the proliferative ability of S2-CP8 cells or the migratory ability of S2-CP8 cells, and exhibiting an exceptional antitumor effect. The ability to develop ELISA methods in which these anti-CKAP4 monoclonal antibodies are used furthermore makes it possible, for example, to measure the serum CKAP4 in pancreatic cancer patients, and therefore also contributes to the development of companion diagnostic agents.

7 Claims, 12 Drawing Sheets

Specification includes a Sequence Listing.

(56) References Cited

OTHER PUBLICATIONS

English Translation of International Search Report, PCT/JP/2018/035719, dated Dec. 25, 2018.

Kimura, Hirokazu et al., "CKAP4 is Dickkopf1 receptor and is involved in tumor progression", J Clin Invest, Jul. 2016, vol. 126, No. 7, pp. 2689-2705.

Kimura, Koichi, May 31, 2017, vol. 32 No. 3 p. 298:502, "method and results", non-official translation (KIMURA, Koichi et al., "New treatment target of pancreatic cancer, DKK1 new receptor CKAP4", The Journal of Japan Pancreas Society).

Kikuchi, Akira et al., "The Dickkopf1-cytoskeleton-associated protein 4 axis creates a novel signalling pathway and may represent a molecular target for cancer therapy", Br J Pharmacol, Jul. 7, 2017, vol. 174, pp. 4651-4665.

Extended European Search Report in EP Patent Application No. 18860970.5 dated Apr. 29, 2021.

Creative Biolabs Cat: "Mouse Anti-CKAP4 Recombinant Antibody (G1/296)", Jan. 1, 2016, pp. 1-2, XP055780814.

Bhavanaski, Dheeraj, et al., "CKAP4 is Identified as a Receptor for Dickkopf in cancer cells", The Journal of Clinical Investigation, vol. 126, No. 7, Jun. 20, 2016, pp. 2419-2421.

Chavda, Burzin, et al., "Antiproliferative factor (APF) binds specifically to sites within the cytoskeleton-associated protein 4 (CKAP4) extracellular domain", BMC Biochemistry, vol. 18, No. 1, Sep. 11, 2017.

Conrads, Thomas P., et al., "CKAP4/p63 is a Receptor for the Frizzled-8 Protein-related Antiproliferative Factor from Interstitial Cystitis Patients," Journal of Biological Chemistry, vol. 281, No. 49, Dec. 8, 2006, pp. 37836-37843.

\* cited by examiner

ANTI-CKAP4 MONOCLONAL ANTIBODY

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 32502639_1.txt, the date of creation of the ASCII text file is Mar. 25, 2020, and the size of the ASCII text file is approximately 5.43 KB. The information in the electronic format of the Sequence Listing is incorporated herein by reference in its entirety.

TECHNICAL FIELD

The present invention relates to an anti-CKAP4 monoclonal antibody that inhibits the binding between DKK1 and CKAP4, and exhibits excellent antitumor effect. The present invention also relates to an antitumor drug including the anti-CKAP4 monoclonal antibody. Further, the present invention relates to a method for measuring CKAP4 using the anti-CKAP4 monoclonal antibody.

BACKGROUND ART

The secretory protein Dikkopf 1 (DKK1) is known as a Wnt signaling suppressor, is a cell proliferation factor that optimizes morphogenesis in the embryonic stage, and has been reported to suppress the proliferation of colon cancer cells after birth. Meanwhile, DKK1 is overexpressed in multiple myeloma, hepatoblastoma, Wilms tumor, prostate cancer, kidney cancer, breast cancer, esophageal cancer, lung cancer and the like, and it is speculated that DKK1 have a function to promote the proliferation of cancer cells. However, the mechanism is unknown.

Under such circumstances, the present inventors have elucidated the signaling pathway of DKK1 enhancing cell proliferation (Non-patent Document 1 and Patent Document 1). Specifically, the inventors have identified, as a result of global analysis of DKK1-binding proteins present in cell membranes, Cytoskeleton-associated protein 4 (CKAP4) as a novel receptor of DKK1. Further, the present inventors have proved, for example, that
(1) PI3K-AKT pathway is activated by binding of DKK1 to CKAP4, and the proliferation of cancer cells is promoted,
(2) both DKK1 and CKAP4 proteins are overexpressed specifically to the tumor region with high frequency in pancreatic cancer, lung cancer, and esophageal cancer, and the pancreatic cancer, lung cancer, and esophageal cancer in which both these proteins are highly expressed show a poor prognosis, and
(3) by suppressing the expression of DKK1 or CKAP4, the activation of AKT in pancreatic cancer cell lines, lung cancer cell lines, and esophageal cancer cell lines in which both DKK1 and CKAP4 proteins are highly expressed is suppressed, and the subcutaneous tumor development in mice is suppressed (Non-patent Document 1 and Patent Document 1). It has also been reported that by inhibiting the binding between DKK1 and CKAP4 by anti-CKAP4 polyclonal antibody, subcutaneous tumor development by pancreatic cancer cell lines, lung cancer cell lines, and esophageal cancer cell lines in mice is successfully suppressed (Non-patent Document 1 and Patent Document 1).

Thus, involvement of CKAP4 in the proliferation of cancer cells has been elucidated, and a molecular target drug that targets CKAP4 is drawing attention as a new antitumor drug.

PRIOR ART DOCUMENTS

Non-Patent Document

Non-Patent Document 1: Hirokazu Kimura et al., J. Clin. Invest., 2016, 126 (7), p. 2689-2705

Patent Document

Patent Document 1: International Publication No. 2016/136372

SUMMARY OF THE INVENTION

Problems to be Solved by the Invention

An anti-CKAP4 monoclonal antibody, which is capable of inhibiting the binding between DKK1 and CKAP4, is useful as a molecular target drug that targets CKAP4. It is important that the anti-CKAP4 monoclonal antibody that targets CKAP4 used as a molecular target drug not only bind to CKAP4, but also inhibit the binding between DKK1 and CKAP4, and effectively suppress the proliferation of cancer cells. However, prior arts have not elucidated which region of CKAP4 is effective to inhibit the binding between DKK1 and CKAP4 and effectively suppress the proliferation of cancer cells by binding of the monoclonal antibody.

Establishment of a method for measuring CKAP4 is also necessary for the development and research of a molecular target drug that targets CKAP4, and the elucidation of pathogenic mechanism and diagnosis of cancers.

Thus, it is an object of the present invention to provide an anti-CKAP4 monoclonal antibody that inhibits the binding between DKK1 and CKAP4, and exhibits excellent antitumor effect. It is another object of the present invention to provide a method for measuring CKAP4.

Means for Solving the Problem

The present inventors have made intensive studies to solve the above-mentioned problems, and, as a result, found that an anti-CKAP4 monoclonal antibody that recognizes at least a part of a region from position 451 to 455, at least a part of a region from position 481 to 485, at least a part of a region from position 502 to 510, at least a part of a region from position 503 to 524 and at least a part of a region from position 585 to 590, or at least a part of a region from position 585 to 592 of an amino acid sequence shown in SEQ ID NO: 1 (the amino acid sequence of CKAP4) as an epitope effectively inhibits the binding between DKK1 and CKAP4, and exhibits excellent antitumor effect. In particular, the present inventors have found that an anti-CKAP4 monoclonal antibody that recognizes at least a part of a region from position 503 to 524 and at least a part of a region from position 585 to 590 of an amino acid sequence shown in SEQ ID NO: 1 as an epitope has remarkably high action of suppressing DKK1-CKAP4 signaling and exhibits remarkably excellent antitumor effect. The anti-CKAP4 monoclonal antibody that recognizes at least a part of a region from position 502 to 510, at least a part of a region from position 503 to 524 and at least a part of a region from position 585 to 590, or at least a part of a region from position 585 to 592 of an amino acid sequence shown in SEQ ID NO: 1 as an epitope cannot be produced by a technique of immunizing a normal mouse using human CKAP4 or a fragment thereof as an immunogen, and has been successfully produced for the first time by a novel technique of immunizing a CKAP4-knockout mouse using human CKAP4 or a fragment thereof as an immunogen. The monoclonal antibody is a novel monoclonal antibody that cannot be easily produced by conventional arts.

The present inventors have also found that human CKAP4 can be quantified by an immunoassay using the anti-CKAP4 monoclonal antibody.

Further studies based on these findings have been made and thereby the present invention has been completed. That is, the present invention provides the invention having the aspects described below.

Item 1. An anti-CKAP4 monoclonal antibody or an antibody fragment thereof that recognizes a site shown in any of (i) to (v) below as an epitope:
  (i) at least a part of a region from position 451 to 455 of an amino acid sequence shown in SEQ ID NO: 1,
  (ii) at least a part of a region from position 481 to 485 of an amino acid sequence shown in SEQ ID NO: 1,
  (iii) at least a part of a region from position 502 to 510 of an amino acid sequence shown in SEQ ID NO: 1,
  (iv) at least a part of a region from position 503 to 524 and at least a part of a region from position 585 to 590 of an amino acid sequence shown in SEQ ID NO: 1, and
  (v) at least a part of a region from position 585 to 592 of an amino acid sequence shown in SEQ ID NO: 1.

Item 2. The anti-CKAP4 monoclonal antibody or an antibody fragment thereof according to item 1, having an isotype of IgG.

Item 3. The anti-CKAP4 monoclonal antibody or an antibody fragment thereof according to item 1 or 2, which is a fully human antibody or a humanized antibody.

Item 4. An antitumor drug including:
  the anti-CKAP4 monoclonal antibody or an antibody fragment thereof according to any of items 1 to 3 as an active ingredient.

Item 5. The antitumor drug according to item 4, which is used for treating lung cancer, pancreatic cancer, or esophageal cancer.

Item 6. Use of an anti-CKAP4 monoclonal antibody or an antibody fragment thereof that recognizes a site shown in any of (i) to (v) below as an epitope for production of an antitumor drug:
  (i) at least a part of a region from position 451 to 455 of an amino acid sequence shown in SEQ ID NO: 1,
  (ii) at least a part of a region from position 481 to 485 of an amino acid sequence shown in SEQ ID NO: 1,
  (iii) at least a part of a region from position 502 to 510 of an amino acid sequence shown in SEQ ID NO: 1,
  (iv) at least a part of a region from position 503 to 524 and at least a part of a region from position 585 to 590 of an amino acid sequence shown in SEQ ID NO: 1, and
  (v) at least a part of a region from position 585 to 592 of an amino acid sequence shown in SEQ ID NO: 1.

Item 7. An anti-CKAP4 monoclonal antibody or an antibody fragment thereof that recognizes a site shown in any of (i) to (v) below as an epitope, which is used for treating a tumor:
  (i) at least a part of a region from position 451 to 455 of an amino acid sequence shown in SEQ ID NO: 1,
  (ii) at least a part of a region from position 481 to 485 of an amino acid sequence shown in SEQ ID NO: 1,
  (iii) at least a part of a region from position 502 to 510 of an amino acid sequence shown in SEQ ID NO: 1,
  (iv) at least a part of a region from position 503 to 524 and at least a part of a region from position 585 to 590 of an amino acid sequence shown in SEQ ID NO: 1, and
  (v) at least a part of a region from position 585 to 592 of an amino acid sequence shown in SEQ ID NO: 1.

Item 8. A method for treating a tumor, including a step of:
  administering an anti-CKAP4 monoclonal antibody or an antibody fragment thereof that recognizes a site shown in any of (i) to (v) below as an epitope to a patient suffering from a tumor:
  (i) at least a part of a region from position 451 to 455 of an amino acid sequence shown in SEQ ID NO: 1,
  (ii) at least a part of a region from position 481 to 485 of an amino acid sequence shown in SEQ ID NO: 1,
  (iii) at least a part of a region from position 502 to 510 of an amino acid sequence shown in SEQ ID NO: 1,
  (iv) at least a part of a region from position 503 to 524 and at least a part of a region from position 585 to 590 of an amino acid sequence shown in SEQ ID NO: 1, and
  (v) at least a part of a region from position 585 to 592 of an amino acid sequence shown in SEQ ID NO: 1.

Item 9. A method for measuring CKAP4, including a step of:
  measuring CKAP4 using the anti-CKAP4 monoclonal antibody or an antibody fragment thereof CKAP4 monoclonal antibody or an antibody fragment thereof according to any of items 1 to 3.

Item 10. The method for measuring CKAP4 according to item 9, wherein the anti-CKAP4 monoclonal antibody or an antibody fragment thereof according to any of claims 1 to 3 is used as at least one of a capture antibody and a detection antibody in ELISA.

Advantages of the Invention

The anti-CKAP4 monoclonal antibody of the present invention effectively inhibits the binding between DKK1 and CKAP4, exhibits an excellent antitumor effect, and thus can be preferably used as a molecular target drug that targets CKAP4 such as an antitumor drug. CKAP4 can be measured quantitatively or qualitatively by using the anti-CKAP4 monoclonal antibody of the present invention. The anti-CKAP4 monoclonal antibody of the present invention has excellent immunoprecipitation capability, can be used for global analysis of CKAP4 binding proteins, and can be an important tool in basic study such as analysis of CKAP4 functions, and search and analysis of functions of CKAP4 binding proteins.

DEPOSIT OF BIOLOGICAL MATERIAL

Figure 1:
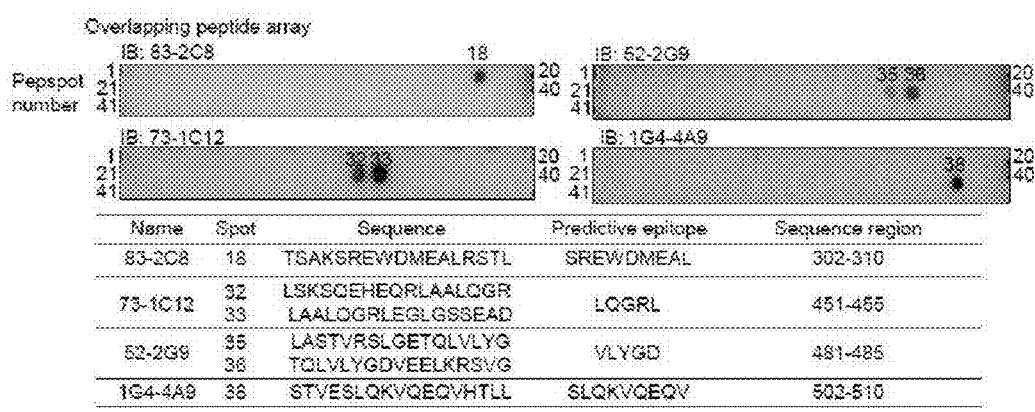
FIG. 1 shows a figure showing the results of epitope identification by epitope mapping analysis for antibodies 83-2C8, 73-1C12, 52-2G9, and 1G4-4A9.

The following biological material has been deposited in accordance with the terms of the Budapest Treaty with the NITE Patent Microorganisms Depositary National Institute of Technology and Evaluation, on the date indicated:

| Biological material | Designation No. | Deposit Date |
|---|---|---|
| 3F11-2B10 | NITE BP-03885 | Apr. 18, 2023 |

Hybridoma 3F11-2B10, was deposited as NITE BP-03885 on Apr. 18, 2023, with the NITE Patent Microorganisms Depositary National Institute of Technology and Evaluation. This deposit was made under the provisions of the Budapest Treaty on the International Recognition of the Deposit of Microorganisms for the Purposes of Patent Procedure and the Regulations there under (Budapest Treaty). This assures maintenance of a viable culture of the deposit for 30 years from date of deposit. The deposit will be made available by the NITE Patent Microorganisms Depositary National Institute of Technology and Evaluation under the terms of the Budapest Treaty, and subject to an agreement between Applicant and the NITE Patent Microorganisms Depositary National Institute of Technology and Evaluation, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited biological material is not to be construed as a license to practice the invention in contravention of the rights granted under the authority of any government in accordance with its patent laws.

EMBODIMENTS OF THE INVENTION

1. Anti-CKAP4 Monoclonal Antibody and Antibody Fragment Thereof

The present invention is an anti-CKAP4 monoclonal antibody and an antibody fragment thereof that recognizes a site shown in any of (i) to (v) below as an epitope: (i) at least a part of a region from position 451 to 455 of an amino acid sequence shown in SEQ ID NO: 1, (ii) at least a part of a region from position 481 to 485 of an amino acid sequence shown in SEQ ID NO: 1, (iii) at least a part of a region from position 502 to 510 of an amino acid sequence shown in SEQ ID NO: 1, and (iv) at least a part of a region from position 503 to 524 and a region from position 585 to 590 of an amino acid sequence shown in SEQ ID NO: 1, (v) at least a part of a region from position 585 to 592 of an amino acid sequence shown in SEQ ID NO: 1. The antibody of the present invention will be described in detail below.

The antibody of the present invention is an antibody that binds to human CKAP4. CKAP4 is known as a transmembrane protein, and the amino acid sequence of human CKAP4 is as shown in SEQ ID NO: 1. In human CKAP4, a region from position 1 to 106 in SEQ ID NO: 1 forms an intracellular domain, a region from position 107 to 127 forms a transmembrane domain, and a region from position 128 to 602 forms an extracellular domain (or a domain inside an endoplasmic reticulum). In human CKAP4, a region from position 1 to 21 in SEQ ID NO: 1 forms an endoplasmic reticulum anchor domain, a region from position 24 to 101 forms a microtubule binding domain, a region from position 318 to 328 forms a tyrosine sulfation region, a region from position 468 to 503 forms a leucine zipper region, and a region from position 525 to 602 forms an α helix region.

The antibody of the present invention recognizes
(i) at least a part of a region from position 451 to 455 (LQGRL) of an amino acid sequence shown in SEQ ID NO: 1,
(ii) at least a part of a region from position 481 to 485 (VLYGD) of an amino acid sequence shown in SEQ ID NO: 1,
(iii) at least a part of a region from position 502 to 510 (SLQKVQEQV) of an amino acid sequence shown in SEQ ID NO: 1,
(iv) at least a part of a region from position 503 to 524 (LQKVQEQVHTLLSQDQAQAARL) and a region from position 585 to 590 (RNDLDR) of an amino acid sequence shown in SEQ ID NO: 1, or
(v) at least a part of a region from position 585 to 592 (RNDLDRLF) of an amino acid sequence shown in SEQ ID NO: 1 as an epitope. Thus, by selecting an anti-CKAP4 monoclonal antibody that recognizes a specific site of CKAP4, binding between DKK1 and CKAP4 can be effectively inhibited and an excellent antitumor effect can be exhibited.

Of the epitopes recognized by the antibody of the present invention, (i) at least a part of a region from position 451 to 455 of an amino acid sequence shown in SEQ ID NO: 1, (ii) at least a part of a region from position 481 to 485 of an amino acid sequence shown in SEQ ID NO: 1, and (iii) at least a part of a region from position 502 to 510 of an amino acid sequence shown in SEQ ID NO: 1 are each recognized as a linear epitope. The "linear epitope" is an epitope in which the primary sequence of amino acids is recognized as an antigen-binding site. The linear epitope recognized by the anti-CKAP4 monoclonal antibody can be identified by epitope mapping analysis using a fragment peptide of CKAP4.

Of the epitopes recognized by the antibody of the present invention, (iv) at least a part of a region from position 503 to 524 and at least a part of a region from position 585 to 590 of an amino acid sequence shown in SEQ ID NO: 1, and (v) at least a part of a region from position 585 to 592 of an amino acid sequence shown in SEQ ID NO: 1 are recognized as a conformational epitope. The "conformational epitope" is not an epitope in which the primary sequence of amino acids is recognized as an antigen-binding site, but an epitope that can be recognized by an antibody when the original conformation of CKAP4 is formed.

In the antibody of the present invention, "the antibody recognizes (iv) at least a part of a region from position 503 to 524 and at least a part of a region from position 585 to 590 of an amino acid sequence shown in SEQ ID NO: 1" means that the antibody recognizes the conformational site formed by both at least a part of a region from position 503 to 524 and at least a part of a region from position 585 to 590 of an amino acid sequence shown in SEQ ID NO: 1 as an epitope. That is, the antibody has poor or no binding capacity to a CKAP4 mutant in which either of a region from position 503 to 524 and a region from position 585 to 590 of an amino acid sequence shown in SEQ ID NO: 1 is deleted. The fact that the antibody recognizes at least a part of a region from position 503 to 524 and at least a part of a region from position 585 to 590 of an amino acid sequence shown in SEQ ID NO: 1 as a conformational epitope can be proved by confirming (1) the antibody does not bind to a fragment peptide consisting of 17 amino acids of CKAP4 contained in position 503 to 590 of an amino acid sequence shown in SEQ ID NO: 1, (2) the antibody has less binding capacity to a CKAP4 mutant in which a region from 585 to 602 is deleted compared to the binding capacity to the CKAP4 mutant in which a region from position 590 to 602 of an amino acid sequence shown in SEQ ID NO: 1 is deleted, (3) the antibody has the same binding capacity to the CKAP4 mutant in which a region from position 585 to 602 of an amino acid sequence shown in SEQ ID NO: 1 is deleted as the binding capacity to the CKAP4 mutant in which the region from position 525 to 602 is deleted, (4) the antibody does not bind to the CKAP4 mutant in which a region from position 503 to 602 is deleted, and (5) the antibody binds to CKAP4 having the original conformation.

Similarly, when the antibody of the present invention recognizes (v) at least a part of a region from position 585 to 592 of an amino acid sequence shown in SEQ ID NO: 1 as an epitope, the amino acid residue present at a position distant from the region in the primary structure may constitute an epitope together with the region. The fact that the antibody recognizes at least a part of a region from position 585 to 592 of an amino acid sequence shown in SEQ ID NO: 1 as a conformational epitope can be proved by confirming (1) the antibody does not bind to a fragment peptide of CKAP4 including position 585 to 592 of an amino acid sequence shown in SEQ ID NO: 1 (for example, a fragment peptide consisting of a region from position 578 to 594 of an amino acid sequence shown in SEQ ID NO: 1), (2) the antibody has less binding capacity to a CKAP4 mutant in which a region from 590 to 602 is deleted compared to the binding capacity to the CKAP4 mutant in which a region from position 592 to 602 of an amino acid sequence shown in SEQ ID NO: 1 is deleted, (3) the antibody does not bind to a CKAP4 mutant in which a region from position 585 to 602 of an amino acid sequence shown in SEQ ID NO: 1 is deleted, and (4) the antibody binds to CKAP4 having the original conformation.

Among the antibodies of the present invention, in particular, the anti-CKAP4 monoclonal antibody that recognizes at least a part of a region from position 503 to 524 and at least a part of a region from position 585 to 590 of an amino acid sequence shown in SEQ ID NO: 1 as an epitope has remarkably high action of suppressing DKK1-CKAP4 signaling, exhibits remarkably excellent antitumor effect, and thus is particularly preferable.

CKAP4 has a characteristic of high sequence conservation between different species. For example, the identity of amino acid sequences between CKAP4 derived from a human and CKAP4 derived from a mouse is as high as about 80%. Due to such sequence conservation, it is difficult to obtain an anti-CKAP4 monoclonal antibody that recognizes at least a part of a region from position 503 to 524 and at least a part of a region from position 585 to 590 of SEQ ID NO: 1, or at least a part of a region from position 585 to 592 of an amino acid sequence shown in SEQ ID NO: 1 as an epitope by immunizing a normal mouse with human CKAP4 (SEQ ID NO: 1). Thus, to obtain the anti-CKAP4 antibody, it is important to immunize a non-human animal (such as a mouse) with CKAP4 knocked out. That is, the anti-CKAP4 monoclonal antibody that recognizes at least a part of a region from position 503 to 524 and at least a part of a region from position 585 to 590 of SEQ ID NO: 1, or at least a part of a region from position 585 to 592 of an amino acid sequence shown in SEQ ID NO: 1 as an epitope is an unique antibody that cannot be obtained by ordinary antibody production techniques, and in fact is capable of recognizing both mouse CKAP4 and human CKAP4.

Though the antibody of the present invention can be a mouse antibody, a rat antibody and the like isolated from an immunized mouse, rat and the like, from the viewpoint of reducing antigenicity in the human body, examples of the antibody preferably include a fully human antibody, a humanized antibody, and a chimeric antibody, further preferably include a fully human antibody and a humanized antibody, and particularly preferably include a fully human antibody.

The "fully human antibody" is an antibody having a structure of the variable regions and the constant regions that are all derived from a human. A "humanized antibody" is an antibody obtained by grafting the complementarity-determining region (CDR) sequence of an antibody derived from a non-human mammal such as a mouse onto the framework sequence of a human antibody, and the sequences other than the CDR sequence are derived from a human antibody. The "chimeric antibody" is an antibody having variable region sequences derived from a mammal other than a human and constant region sequences derived from a human, and examples thereof include a mouse-human chimeric antibody having variable region sequences derived from a mouse antibody and constant region sequences derived from a human antibody. The method for producing a fully human antibody, a humanized antibody, and a chimeric antibody has been established, and these antibodies can be produced by known techniques.

The isotype of the antibody of the present invention is not particularly limited, and can be, for example, IgG (IgG$_1$, IgG$_2$, IgG$_3$, and IgG$_4$), IgA (IgA$_1$ and IgA$_2$), IgM, IgD, IgE or the like. However, IgG is preferable.

The antibody fragment of the present invention can be an antibody fragment having at least a CDR for recognizing and binding the epitope, and examples thereof include Fab, Fab', F(ab')$_2$, scFv, and scFv-Fc.

The antibody and an antibody fragment thereof of the present invention can be obtained according to a known antibody production technique. Specifically, the antibody of the present invention can be obtained according to a method of producing a monoclonal antibody including a step of immunizing a non-human animal such as a mouse using CKAP4, the extracellular domain (or the domain inside an endoplasmic reticulum) of CKAP4 (position 128 to 602 of an amino acid sequence shown in SEQ ID NO: 1), or a peptide containing the epitope. Because the homology of the amino acid sequence of CKAP4 between a mouse and a human is high, it is difficult to obtain an anti-CKAP4 antibody that recognizes at least a part of a region from position 503 to 524 and at least a part of a region from position 585 to 590 of SEQ ID NO: 1, or at least a part of a region from position 585 to 592 of an amino acid sequence shown in SEQ ID NO: 1 as an epitope by immunizing a normal mouse. Thus, an anti-CKAP4 antibody that recognizes at least a part of a region from position 503 to 524 and at least a part of a region from position 585 to 590 of SEQ ID NO: 1, or at least a part of a region from position 585 to 592 of an amino acid sequence shown in SEQ ID NO: 1 as an epitope can be obtained by immunizing a mouse with CKAP4 knocked out with CKAP4 or an extracellular domain of CKAP4. The epitope that the obtained antibody recognizes can be proved by confirming the antigen-binding site by the above-mentioned method. A fully human antibody, a humanized antibody, or chimeric antibody can also be obtained by a known production technique.

2. Antitumor Drug

The antitumor drug of the present invention includes the anti-CKAP4 monoclonal antibody or an antibody fragment thereof as an active ingredient. The antitumor drug of the present invention will be described in detail below.

(Active Ingredient)

In the antitumor drug of the present invention, the anti-CKAP4 monoclonal antibody or an antibody fragment thereof is used as an active ingredient.

(Use)

As disclosed in Patent Document 1, because CKAP4 is expressed in cancer cells and promotes the proliferation of cancer cells, the antitumor drug of the present invention can suppress the proliferation of cancer cells by suppressing the expression or function of CKAP4. Thus, the antitumor drug of the present invention can be used for treating cancer. The cancers that can be treated by the antitumor drug of the present invention are not particularly limited, and specific examples thereof include solid cancers such as lung cancer, pancreatic cancer, esophageal cancer, colon cancer, large intestine cancer, stomach cancer, rectum cancer, liver cancer, breast cancer, bladder cancer, prostate cancer, cervical cancer, head and neck cancer, bile duct cancer, gallbladder cancer, oral cancer, tongue cancer, pharyngeal cancer, laryngeal cancer, brain tumor, glioma, glioblastoma, glioblastoma multiforme, and peritoneal metastasis; and blood cancers such as leukemia and malignant lymphoma.

As disclosed in Patent Document 1, a drug of an anti-CKAP4 monoclonal antibody or an antibody fragment thereof effectively exhibits an effect of suppressing the proliferation of cancer cells to cancer cells expressing CKAP4, in particular, cancer cells expressing both CKAP4 and DKK1, and thus the antitumor drug of the present invention is preferably used for cancer cells expressing CKAP4, in particular, cancer cells expressing both CKAP4 and DKK1. Among cancers, lung cancer, pancreatic cancer, and esophageal cancer have high expression of CKAP4 and DKK1 with high frequency, and thus are particularly preferable as cancers that can be treated with the antitumor drug of the present invention.

The CKAP4 expression in cancer can be confirmed by tissue immunization of the collected cancer tissue. Specifically, the collected cancer tissue is immunostained with an anti-CKAP4 antibody, and CKAP4 is judged to be expressed when the CKAP4 expression is observed in 5% or more of the tumor region. Preferable examples of cancers that can be treated with the antitumor drug of the present invention include cancers having CKAP4 expression in 5% or more of the tumor region, further preferably include cancers having CKAP4 expression in 20% or more of the tumor region, and particularly preferably include cancers having CKAP4 expression in 50% or more of the tumor region.

CKAP4 expression in cancer can be measured by collecting RNA from collected cancer tissues and subjecting the RNA to quantitative PCR. In this case, the determination of the presence or absence of CKAP4 expression can be performed using the non-cancerous tissue of the same case as an index. Specifically, CKAP4 is judged to be highly expressed in the cancer when the amount of CKAP4 in the cell lysate of the cancer tissue is higher than the amount of CKAP4 in the cell lysate of the non-cancerous tissue of the same case.

Similar to the case of CKAP4, DKK1 expression in cancer can be confirmed by, for example, a method of tissue immunization of the collected cancer tissue, and a method of measuring the DKK1 expression by collecting RNA from collected cancer tissues and subjecting the RNA to quantitative PCR.

Specifically, the collected cancer tissue is immunostained with an anti-DKK1 antibody, and DKK1 is judged to be expressed when the DKK1 expression is observed in 5% or more of the tumor region. Preferable examples of cancers that can be treated with the antitumor drug of the present invention include cancers having DKK1 expression in 5% or more of the tumor region, further preferably include cancers having DKK1 expression in 20% or more of the tumor region, and particularly preferably include cancers having DKK1 expression in 50% or more of the tumor region.

When DKK1 is measured by collecting RNA from the collected cancer tissues, DKK1 is judged to be highly in the cancer when the amount of DKK1 in the cell lysate of the cancer tissue is higher than the amount of DKK1 in the cell lysate of the non-cancerous tissue of the same case.

(Administration Method)

The administration method of the antitumor drug of the present invention can be oral administration or parenteral administration as long as an antitumor effect is obtained. Specific examples of the administration method of the antitumor drug of the present invention include oral administration; and parenteral administration such as injection administration (intravenous injection, subcutaneous injection, intramuscular injection, intraperitoneal injection, local injection into the affected area and the like) and suppository administration, and preferably include injection administration.

The dosage of the antitumor drug of the present invention can be suitably set according to the giving method, the type of the cancer that is treated, the degree of the symptom of the patient and the like. For example, when a nucleic acid molecule is used as an active ingredient, as a single dose of the nucleic acid molecule, about 0.01 μg to 1000 mg/kg body weight, preferably about 0.1 to 100 μg/kg body weight can be usually administered. For example, as a single dose of the anti-CKAP4 monoclonal antibody or an antibody fragment thereof, about 0.1 mg to 20 mg/kg body weight can be usually administered with a frequency of about once every 1 to 3 weeks.

The antitumor drug of the present invention can be used alone or in combination with one or two or more other drugs having antitumor activity and/or radiation therapy. An example of other drugs used in combination with the antitumor drug of the present invention is an antitumor drug used in chemotherapy. Specific examples of such an antitumor drug include an antimetabolite, an alkylating drug, an anti-microtubule drug, an anticancer antibiotic, a topoisomerase inhibitor, and a platinum preparation. Specific examples thereof include antimetabolites such as gemcitabine, 5-fluorouracil, methotrexate, doxyfluridine, tegafur, 6-mercaptopurine, and cytarabine;

alkylating drugs such as clophosphamide, ifosfamide, thiotepa, carbone, and nimustine hydrochloride;

anti-microtubule drugs such as docetaxel, paclitaxel, vincristine, vindesine, and vinorelbine;

anticancer antibiotics such as doxorubicin hydrochloride, mitomycin, amrubicin hydrochloride, pirarubicin hydrochloride, epirubicin hydrochloride, aclarubicin hydrochloride, mitoxantrone hydrochloride, bleomycin hydrochloride, and pepromycin sulfate;

topoisomerase inhibitors such as irinotecan and nogitecan hydrochloride; and platinum preparations such as cisplatin, oxaliplatin, carboplatin, and nedaplatin. Among these, antimetabolites (in particular, gemcitabine) are preferable because they can remarkably increase the antitumor effect when used in combination with the antitumor drug of the present invention.

(Dosage Form)

The antitumor drug of the present invention is prepared in a dosage form corresponding to the administration method. Examples of the dosage form of the antitumor drug of the present invention include liquid preparations such as liquid medicines, suspensions, emulsions, and injections; and solid preparations such as tablets, capsules, pills, powders, granules, and suppositories.

The antitumor drug of the present invention is formulated by adding a pharmaceutically acceptable carrier or additive depending on the dosage form. For example, in the case of a liquid preparation, the antitumor drug of the present invention can be formulated using physiological saline, a buffer and the like. In the case of a solid preparation, the antitumor drug of the present invention can be formulated using an excipient, a binder, a disintegrant, a lubricant and the like.

3. Method for Measuring CKAP4

The method for measuring CKAP4 of the present invention includes a step of measuring CKAP4 using the anti-CKAP4 monoclonal antibody or an antibody fragment thereof. The method for measurement of the present invention will be described in detail below.

In the method for measurement of the present invention, CKAP4 in a sample is immunoassayed using an antigen-antibody reaction between the anti-CKAP4 monoclonal antibody or an antibody fragment thereof and CKAP4 in a sample.

The sample is not particularly limited as long as the measurement of CKAP4 can be performed, and examples thereof include biological samples such as blood, serum, plasma, urine, spinal fluid, ascites, various tissues, various tissue fluids, and purified exosomes, and a medium.

The method for measurement of the present invention can be performed in any immunoassay including sandwich ELISA, exosome ELISA, competition method, and aggregation method. The method for measurement of the present invention can also be used for immunostaining of living tissues.

In sandwich ELISA, a capture antibody that captures an antigen and a detection antibody that binds to the antigen bound to the capture antibody are used. When sandwich method is employed in the method for measurement of the present invention, the anti-CKAP4 monoclonal antibody or an antibody fragment thereof is used as at least one of the capture antibody and the detection antibody. In particular, from the viewpoint of measuring CKAP4 with higher accuracy, an anti-CKAP4 monoclonal antibody or an antibody fragment thereof that recognizes at least a part of a region from position 503 to 524 and at least a part of a region from position 585 to 590 of an amino acid sequence shown in SEQ ID NO: 1 as epitopes is preferably used as at least one of a capture antibody and a detection antibody.

Examples of the preferable aspect in the case where sandwich ELISA is employed in the method for measurement of the present invention include an aspect in which one type of the anti-CKAP4 monoclonal antibody or an antibody fragment thereof is used as a capture antibody, and another type of the anti-CKAP4 monoclonal antibody or an antibody fragment thereof (one that recognizes a different epitope from the epitope recognized by the anti-CKAP4 monoclonal antibody or an antibody fragment thereof used as the capture antibody) is used as a detection antibody; further preferably include an aspect in which an anti-CKAP4 monoclonal antibody or an antibody fragment thereof that recognizes at least a part of a region from position 503 to 524 and at least a part of a region from position 585 to 590 of an amino acid sequence shown in SEQ ID NO: 1 as an epitope is used as a capture antibody, and an anti-CKAP4 monoclonal antibody or an antibody fragment thereof that recognizes at least a part of a region from position 451 to 455, at least a part of a region from position 481 to 485, or at least a part of a region from position 502 to 510 of an amino acid sequence shown in SEQ ID NO: 1 as an epitope is used as a detection antibody; and particularly preferably include an aspect in which an anti-CKAP4 monoclonal antibody or an antibody fragment thereof that recognizes at least a part of a region from position 503 to 524 and at least a part of a region from position 585 to 590 of an amino acid sequence shown in SEQ ID NO: 1 as an epitope is used as a capture antibody, and an anti-CKAP4 monoclonal antibody or an antibody fragment thereof that recognizes at least a part of a region from position 502 to 510 of an amino acid sequence shown in SEQ ID NO: 1 as an epitope is used as a detection antibody.

Exosome ELISA is an analysis for measuring CKAP4 in exosomes by reacting and immobilizing exosomes onto a plate on which a protein that specifically binds to a molecule present (for example, phosphatidylserine and so on) on the surface of exosomes, and then using one type of the anti-CKAP4 monoclonal antibody or an antibody fragment thereof as a detection antibody. Examples of the detection antibody used in exosome ELISA particularly preferably include an anti-CKAP4 monoclonal antibody or an antibody fragment thereof that recognizes at least a part of a region from position 585 to 592 of an amino acid sequence shown in SEQ ID NO: 1 as an epitope.

Immunoassay includes, based on the type of labels, enzyme-linked immunoassay (ELISA), fluoroimmunoassay, fluorescent immunoassay, and radioisotope immunoassay, and any of these can be used in the method for measurement of the present invention. From the viewpoint of simplicity and rapidity of measurement, enzyme-linked immunoassay is preferable.

Immunoassays themselves in which antigen-antibody reaction is used are known, and the method for measurement of the present invention can be performed by known techniques according to the measurement principle of immunoassay and the type of labels.

It is known that the presence or absence of CKAP4 in exosomes collected from a subject can be used as an index to determine whether the subject suffers from cancer, and thus exosome ELISA in which a CKAP4 antibody of a fragment thereof of the present invention is used can be used for measurement of CKAP4 in exosomes collected from the subject for cancer tests. The type of cancer to be tested is not particularly limited, and specific examples thereof include solid cancers such as lung cancer, pancreatic cancer, colon cancer, large intestine cancer, stomach cancer, rectum cancer, liver cancer, breast cancer, bladder cancer, prostate cancer, cervical cancer, head and neck cancer, bile duct cancer, gallbladder cancer, oral cancer, tongue cancer, pharyngeal cancer, laryngeal cancer, brain tumor, glioma, glioblastoma, and glioblastoma multiforme; and blood cancers such as leukemia and malignant lymphoma. Among these, lung cancer, pancreatic cancer, and esophageal cancer are preferable. The origin of exosomes used for cancer tests is not particularly limited, and examples thereof include body fluids such as a serum and urine. Among these, the serum is preferable.

It is known that the presence or absence of CKAP4 in a blood sample collected from a subject can be used as an index to determine whether the subject suffers from cancer, and thus sandwich ELISA in which an CKAP4 antibody of a fragment thereof of the present invention is used can be used for measurement of CKAP4 in a blood sample collected from the subject for cancer tests. The type of cancer to be tested is not particularly limited, and specific examples thereof include solid cancers such as lung cancer, pancreatic cancer, colon cancer, large intestine cancer, stomach cancer, rectum cancer, liver cancer, breast cancer, bladder cancer, prostate cancer, cervical cancer, head and neck cancer, bile duct cancer, gallbladder cancer, oral cancer, tongue cancer, pharyngeal cancer, laryngeal cancer, brain tumor, glioma, glioblastoma, and glioblastoma multiforme; and blood cancers such as leukemia and malignant lymphoma. Among these, lung cancer, pancreatic cancer, and esophageal cancer are preferable. Examples of blood samples used for cancer tests include a serum and plasma, and preferably a serum.

The expression level of CKAP4 in a cancer tissue is known to correlate with the postoperative prognosis of cancer patients, and thus the method for measurement of the present invention can be used for measurement of the expression level of CKAP4 in a cancer tissue collected from a cancer patient for testing the postoperative prognosis of the cancer patient. The type of cancer to be tested for the prognosis is not particularly limited, and specific examples thereof include solid cancers such as lung cancer, pancreatic cancer, colon cancer, large intestine cancer, stomach cancer, rectum cancer, liver cancer, breast cancer, bladder cancer, prostate cancer, cervical cancer, head and neck cancer, bile duct cancer, gallbladder cancer, oral cancer, tongue cancer, pharyngeal cancer, laryngeal cancer, brain tumor, glioma, glioblastoma, and glioblastoma multiforme; and blood cancers such as leukemia and malignant lymphoma. Among these, lung cancer, pancreatic cancer, and esophageal cancer are preferable.

Further, the present invention also provides a measuring kit used in the method for measurement. The measuring kit of the present invention includes the anti-CKAP4 monoclonal antibody or an antibody fragment thereof.

In addition to the anti-CKAP4 monoclonal antibody or an antibody fragment thereof, the measuring kit of the present invention can further include other reagents and instruments according to the measurement principle of immunoassay and the type of labels. For example, when enzyme-linked immunoassay is selected, the measuring kit of the present invention can include, in addition to the anti-CKAP4 monoclonal antibody or an antibody fragment thereof, a measurement plate, a substrate solution, a reaction stop solution, a washing solution, and a standard solution. When the sandwich ELISA is employed, the anti-CKAP4 monoclonal antibody or antibody fragment thereof used as a capture antibody can be provided in a state where the anti-CKAP4 monoclonal antibody or antibody fragment thereof is immobilized on a solid phase.

The measuring kit of the present invention can be used as a test kit for cancer or a test kit for the postoperative prognosis of cancer patients.

EXAMPLES

Though the present invention will be described in detail below based on experimental data, the present invention is not limited thereto.

1. Production of Anti-CKAP4 Monoclonal Antibody

A mouse monoclonal antibody that specifically recognizes CKAP4 was produced by iliac lymph node method or spleen method.

In the iliac lymph node method, 0.7 mg/mL of a fusion protein in which glutathione S-transferase (GST) and the extracellular domain of human CKAP4 (a polypeptide consisting of amino acid residues from position 128 to 602 of an amino acid sequence shown in SEQ ID NO: 1) are fused, and 100 μL of emulsion containing complete Freund's adjuvant were injected to a tail head of a 10-week-old female mouse (wild type) to immunize it. Further, 17 days after the first injection for immunization, 100 μL of an emulsion containing 0.7 mg/mL of the fusion protein was injected to the tail head for a booster. Four days after the booster, cells were collected from the iliac lymph node of the immunized mouse and fused with mouse myeloma-derived myeloma Sp2/0-Ag14 cells in 50% polyethylene glycol to obtain a hybridoma.

In the spleen method, 1 mg/mL of a fusion protein in which glutathione S-transferase (GST) and the C-terminus of the extracellular domain of human CKAP4 (a polypeptide consisting of amino acid residues from position 468 to 602 of an amino acid sequence shown in SEQ ID NO: 1) are fused, and 100 μL of emulsion containing complete Freund's adjuvant were intraperitoneally injected to an eight-week-old mouse with CKAP4 knocked out to immunize it. Further, every 14 days from the first injection for immunization, a total of four times, 100 μL of an emulsion containing 1 mg/mL of the fusion protein was intraperitoneally injected for a booster. Fourteen days after the final booster, cells were collected from the spleen of the immunized mouse and fused with mouse myeloma-derived myeloma Sp2/0-Ag14 cells in 50% polyethylene glycol to obtain a hybridoma.

The obtained hybridoma was seeded in a 96-well plate and cultured in HAT selection medium. Then, the hybridoma that produces the anti-CKAP4 antibody was identified by performing measurement by ELISA, detection of endogenous CKAP4 by Western blotting, immunostaining of CKAP4 on the cell surface, and measurement of inhibition capability for binding between DKK1 and CKAP4 using the conditioned medium of the hybridoma.

As a result, as hybridoma clones that produce the anti-CKAP4 monoclonal antibody, three strains were finally obtained by the iliac lymph node method, and 3 strains by the spleen method. The anti-CKAP4 monoclonal antibodies obtained from the three strains of the hybridoma clones obtained by the iliac lymph node method were named 83-2C8, 73-1C12, and 52-2G9, respectively. The anti-CKAP4 monoclonal antibodies obtained from the three strains of the hybridoma clones obtained by the spleen method were named 1G4-4A9, 3F11-2B10, and 5A6-17A11, respectively.

The isotypes of the obtained anti-CKAP4 monoclonal antibodies were identified using a mouse isotyping kit, and confirmed to be IgG2b (k) for antibodies 83-2C8, 73-1C12, 1G4-4A9, and 3F11-2B10, and IgG2a (k) for antibodies 52-2G9 and 5A6-17A11.

2. Identification of Epitope of Anti-CKAP4 Monoclonal Antibody

The epitope of the obtained anti-CKAP4 monoclonal antibodies was identified. Specifically, epitope mapping analysis was performed using a peptide array (PepSpot) in which a fragment peptide of human CKAP4 (each peptide has 17 amino acid residues, and the neighboring peptide has overlapping seven amino acid residues) is immobilized on a cellulose membrane. As a result, as shown in FIG. 1, it was proved that antibody 83-2C8 recognizes a region from position 302 to 310 of SEQ ID NO: 1, antibody 73-1C12 recognizes a region from position 451 to 455 of SEQ ID NO: 1, antibody 52-2G9 recognizes a region from position 481 to 485 of SEQ ID NO: 1, and antibody 1G4-4A9 recognizes a region from position 502 to 510 of SEQ ID NO: 1 as an epitope. Meanwhile, the epitope recognized by antibodies 3F11-2B10 and 5A6-17A11 was not identified by epitope mapping analysis. That is, the results suggest that antibodies 3F11-2B10 and 5A6-17A11 recognize a conformational epitope.

Figure 2:
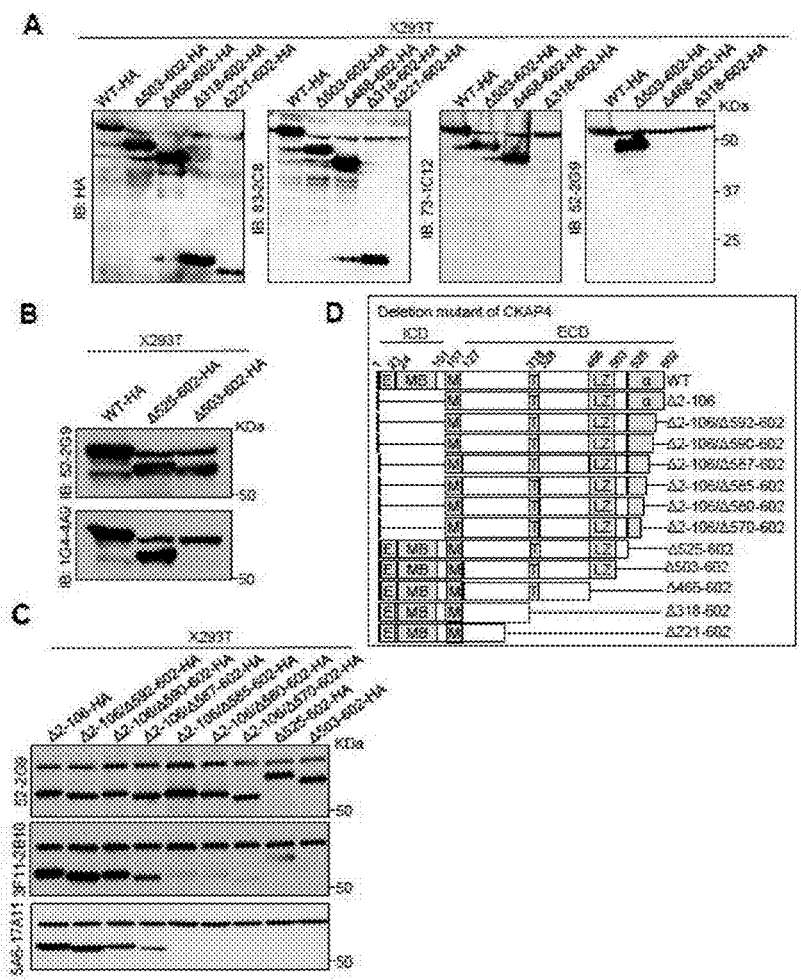
FIG. 2A shows a figure showing the results of immunoblotting (IB) performed on a deletion mutant of human CKAP4 using anti-HA antibody, antibodies 83-2C8, 73-1C12, and 52-2G9.
FIG. 2B shows a figure showing the results of immunoblotting performed on a deletion mutant of human CKAP4 using antibodies 52-2G9 and 1G4-4A9.
FIG. 2C shows a figure showing the results of immunoblotting performed on a deletion mutant of human CKAP4 using antibodies 52-2G9, 3F11-2B10, and 5A6-17A11.
FIG. 2D shows a figure showing the amino acid sequence of the deletion mutant of human CKAP4 used.

Fetal normal kidney cells (X293T cells) that transiently express polypeptides of wild-type human CKAP4 (SEQ ID NO: 1, WT) and deletion mutants of wild-type human CKAP4 (Δ2-106, Δ2-106/Δ592-602, Δ2-106/Δ587-602, Δ2-106/582-602, Δ525-602, Δ503-602, Δ468-602, Δ318-602, and Δ221-602) fused with an HA tag shown in FIG. 2D was produced. The cell lysate of the X293T cells was subjected to immunoblotting using an anti-CKAP4 monoclonal antibody and an anti-HA antibody. The results are shown in FIG. 2A to 2C. For the results such as (i) antibody 83-2C8 was capable of detecting Δ318-602, but not capable of detecting Δ221-602, (ii) antibody 73-1C12 was capable of detecting Δ468-602, but not capable of detecting Δ318-602, (iii) antibody 52-2G9 was capable of detecting Δ503-602, but not was capable of detecting Δ468-602, and (iv) antibody 1G4-4A9 was capable of detecting Δ525-602, but not was capable of detecting Δ503-602, the binding properties of these antibodies to CKAP4 deletion mutants were as expected from the results of the epitopes identified above. Meanwhile, antibody 3F11-2B10 showed lowered detectability for Δ587-602, further lowered detectability for Δ585-602 compared to Δ587-602, and detectability for Δ580-602, Δ570-602, and Δ525-602 similar to that for Δ585-602, and thus antibody 3F11-2B10 is thought to recognize a region including position 585 to 590 of SEQ ID NO: 1 as a conformational epitope. However, antibody 3F11-2B10 was capable of detecting Δ525-602 even though the detectability was low, but was not capable of detecting Δ503-602. These results show that antibody 3F11-2B10 also recognizes a region including position 503 to 524 of SEQ ID NO: 1 as a conformational epitope. Thus, the antibody 3F11-2B10 was confirmed to recognize a region including position 503 to 524 and 585 to 590 of SEQ ID NO: 1 as a conformational epitope. Antibody 5A6-17A11 had lowered detectability for Δ590-602, was not capable of detecting Δ585-602, and thus was confirmed to recognize a region including position 585 to 592 of SEQ ID NO: 1 as a conformational epitope.

Figure 3:
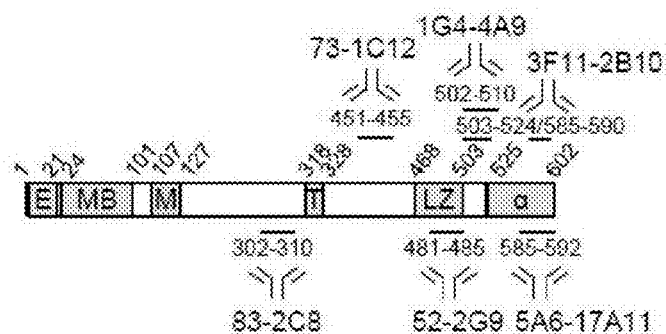
FIG. 3 shows a summary image diagram schematically showing epitopes of antibodies 83-2C8, 73-1C12, 52-2G9, 1G4-4A9, 3F11-2B10, and 5A6-17A11.

FIG. 3 shows a summary image diagram schematically showing the epitope of each anti-CKAP4 monoclonal antibody based on the results above. In the schematic diagram of the sequence of CKAP4 shown in FIG. 3, E represents the endoplasmic reticulum anchor domain, MB represents the microtubule binding domain, M represents the transmembrane domain, T represents the tyrosine sulfation region, LZ represents the leucine zipper region, and a represents the alpha helix region.

3. Verification of Cross-Reactivity of Anti-CKAP4 Monoclonal Antibody to Non-Human-Derived CKAP4

The cross-reactivity of the obtained anti-CKAP4 monoclonal antibody to human, dog, and mouse-derived CKAP4 was verified. Specifically, lysates (Input) of human pancreatic cancer cells (S2-CP8 cells), mouse mammary epithelial cells (Eph4 cells), and dog kidney tubular epithelial cells (MDCK cells) were subjected to immunoblotting (IB) using 1 μg/mL of an anti-CKAP4 monoclonal antibody or anti-CKAP4 polyclonal antibody.

Figure 4:
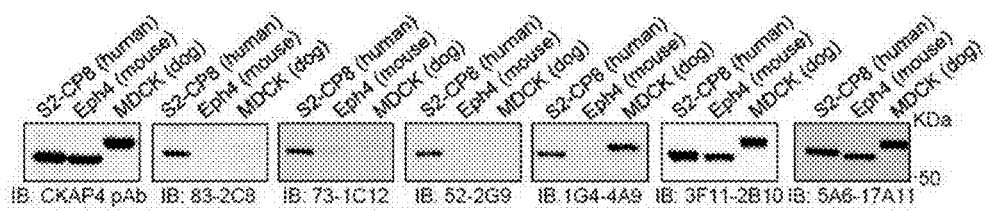
FIG. 4 shows a figure showing the results of immunoblotting (IB) performed on CKAP4 derived from a human, a dog, and a mouse using antibodies 83-2C8, 73-1C12, 52-2G9, 1G4-4A9, 3F11-2B10, 5A6-17A11, and anti-CKAP4 polyclonal antibody.

The obtained results are shown in FIG. 4. Antibodies 83-2C8, 73-1C12, and 52-2G9 bound only to human CKAP4, and did not bind to dog or mouse CKAP4. Antibody 1G4-4A9 bound to human CKAP4 and dog CKAP4, and did not bind to mouse CKAP4. Antibodies 3F11-2B10 and 5A6-17A11 bound to all of human, dog, and mouse CKAP4.

4. Detection of CKAP4 on Cell Surface Using Anti-CKAP4 Monoclonal Antibody

Figure 5:
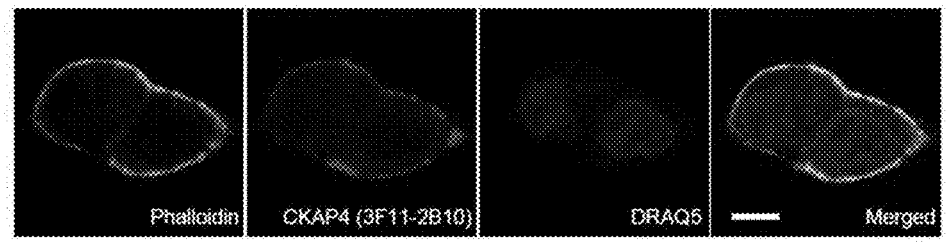
FIG. 5 shows a figure showing the results of detection of CKAP4 on the surface of S2-CP8 cells using antibody 3F11-2B10.

The surface (Non-permeabilized) of S2-CP8 cells was immunostained with antibody 3F11-2B10 (red) and anti-phalloidin antibody (green), and the nucleus was stained with DRAQ5 DNA Dye (blue). The results are shown in FIG. 5. The results confirmed that CKAP4 present on the cell surface can be detected by using antibody 3F11-2B10.

5. Measurement of Binding Capacity of Anti-CKAP4 Antibody to CKAP4

(Preparation of Sample Solution)

Biotin-labeled anti-CKAP4 monoclonal antibodies (antibodies 83-2C8, 73-1C12, 52-2G9, 1G4-4A9, 3F11-2B10, and 5A6-17A11) were diluted with PBS containing 1% BSA to prepare sample solutions having a concentration of 0.125, 0.25, 0.5, 1, 2.5, and 5 nM.

(Measurement by ELISA)

A polypeptide (GST-CKAP4-ECD) (a variant with intracellular domain deleted) in which glutathione-S-transferase (GST) is linked to the N-terminus of the extracellular domain (ECD) of CKAP4 (position 128 to 602 of an amino acid sequence shown in SEQ ID NO: 1) was prepared. To each well of a 96-well plate (9018, Corning), 100 μL of a solution containing 1 nm of GST-CKAP4-ECD or GST was added and incubated overnight at room temperature. Then, after washing with PBS containing 0.05% Tween 20, blocking solution (PBS containing 1% BSA) was added to each well and the well was incubated at room temperature for one hour. Then, the well was washed with PBS containing 0.05% Tween 20, 50 μL of a sample solution was added to each well, and the well was incubated at room temperature for one hour. After washing, 50 μL of HRP (horseradish peroxidas)-streptavidin (DY998, R & D Systems, Inc., Minneapolis, MN) solution was added to each well and the well was incubated at room temperature for 20 minutes. Then, a substrate solution (DY999, R & D Systems, Inc., Minneapolis, MN) was added to each well and allowed to react for 10 minutes. The reaction was stopped by adding 50 μL of a reaction stop solution (Cell Signaling Technology, Beverly, MA) to each well, and absorbances at wavelengths of 450 nm and 540 nm were measured with a microplate reader.

(Result)

Figure 6:
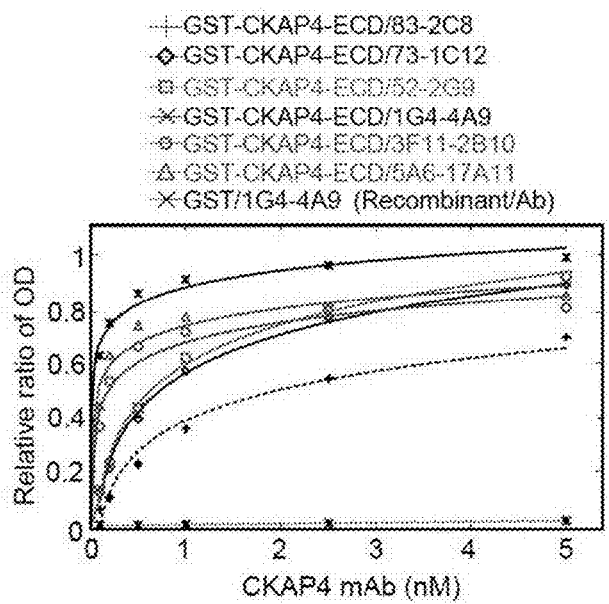
FIG. 6 shows a figure showing the results of measurement of the binding capacity of antibodies 83-2C8, 73-1C12, 52-2G9, 1G4-4A9, 3F11-2B10, and 5A6-17A11 to the extracellular domain (ECD) of CKAP4.

The results are shown in FIG. 6. A value obtained by subtracting the absorbance at 540 nm from the absorbance at a wavelength of 450 nm is shown in the longitudinal axis in FIG. 6. The average value of three measurement results is shown. The results confirmed that antibodies 83-2C8, 73-1C12, 52-2G9, 1G4-4A9, 3F11-2B10, and 5A6-17A11 bind to the extracellular domain (ECD) of CKAP4 in a concentration-dependent manner. Antibody 1G4-4A9 had the highest binding capacity to CKAP4, and antibody 83-2C8 had the lowest binding capacity to CKAP4.

6. Evaluation of Inhibition Capability of the Binding Between DKK1 and CKAP4

Figure 7:
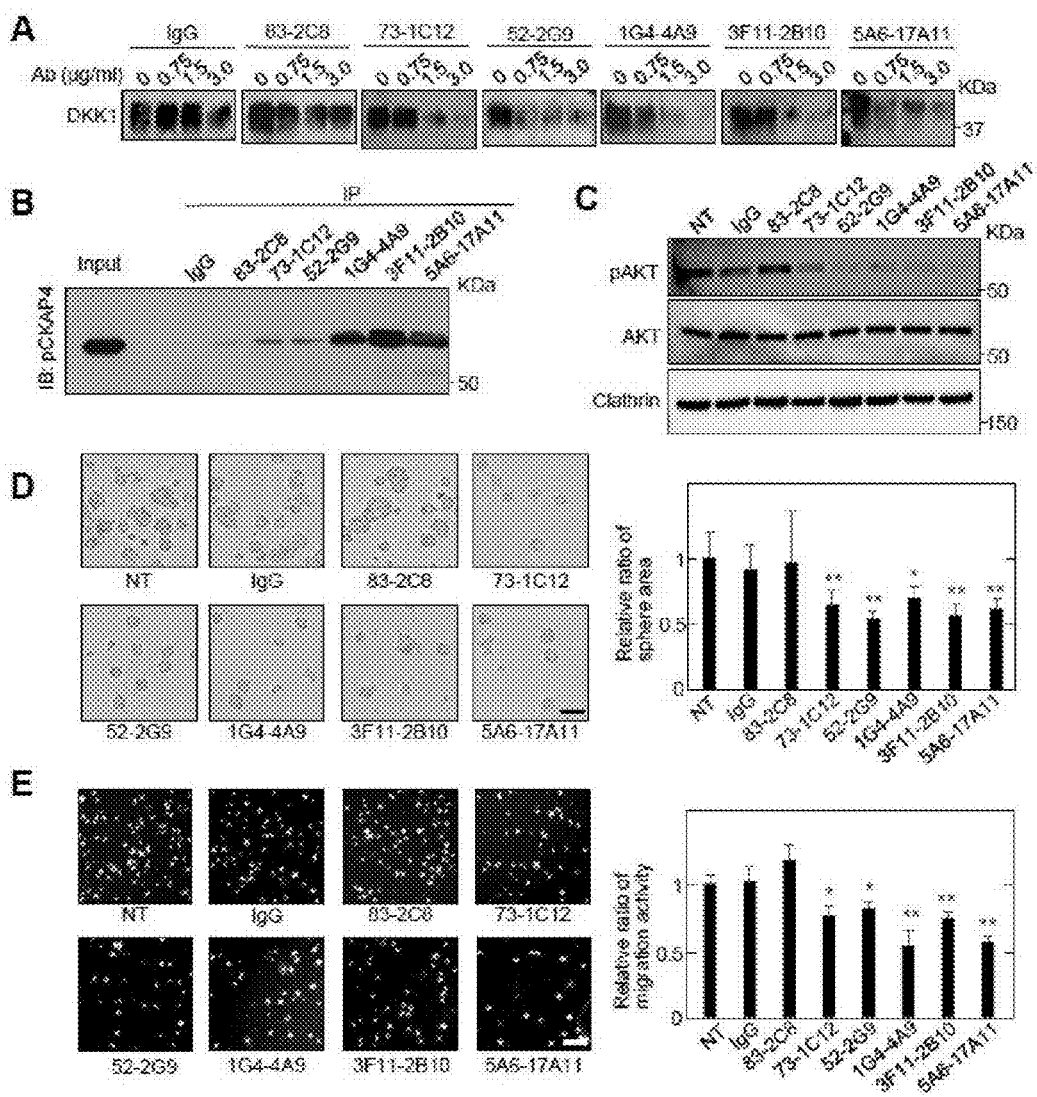
FIG. 7A shows a figure showing the results of evaluation of the inhibition capability of the binding between CKAP4 and DKK1 using the anti-CKAP4 monoclonal antibodies.
FIG. 7B shows a figure showing the results of evaluation of the immunoprecipitation capability using the anti-CKAP4 monoclonal antibodies.
FIG. 7C shows a figure showing the results of evaluation of the inhibition capability of the AKT activity in human pancreatic cancer cells (S2-CP8 cells) of the anti-CKAP4 monoclonal antibodies.
FIG. 7D shows a figure showing the results of evaluation of the inhibition capability of the proliferation of S2-CP8 cells under three-dimensional culture using the anti-CKAP4 monoclonal antibodies.
FIG. 7E shows a figure showing the results of evaluation of the inhibition capability of the migration of S2-CP8 cells using the anti-CKAP4 monoclonal antibodies.

A polypeptide (GST-CKAP4-ECD) (a variant with intracellular domain deleted) in which glutathione-S-transferase (GST) is linked to the N-terminus of the extracellular domain (ECD) of CKAP4 (position 128 to 602 of an amino acid sequence shown in SEQ ID NO: 1) was prepared. In 500 μL of NP40 buffer, 2 nM of GST-CKAP4-ECD and 0.75 to 3.0 μg/mL of an anti-CKAP4 monoclonal antibody or control IgG (manufactured by FUJIFILM Wako Pure Chemical Corporation, normal mouse IgG, code No. 140-09511) were mixed, then 2 nM of DKK1-FLAG (a fusion protein in which FLAG tag is added to human DKK1) was added, and the mixture was allowed to react at 4° C. for two hours. Then, proteins were collected using agarose carrying glutathione, and DKK1 was detected using anti-DKK1 antibody. The results are shown in FIG. 7A. The results confirmed that antibodies 73-1C12, 52-2G9, 1G4-4A9, 3F11-2B10 and 5A6-17A11 have higher inhibition capability of the binding between the extracellular domain of CKAP4 and DKK1 than antibody 83-2C8.

7. Verification of Effect of Anti-CKAP4 Antibody on Internalization of CKAP4

Figure 8:
FIG. 8A shows a figure showing the results of detection of CKAP4 in a cell membrane (PM) and a cell lysate (lysates) after an anti-CKAP4 monoclonal antibody, control IgG, or DKK1-FLAG was added to S2-CP8 cells with DKK1 knocked out (S2-CP8/DKK1 KO cells), and the cells were cultured for a predetermined time.
FIG. 8B shows a figure showing the results of detection of CKAP4 in a cell membrane (PM) and a cell lysate (lysates) after S2-CP8/DKK1 KO cells were cultured in a medium containing an anti-CKAP4 monoclonal antibody or control IgG, DKK1-FLAG was further added, and the cells were cultured for a predetermined time.
Figure 8:
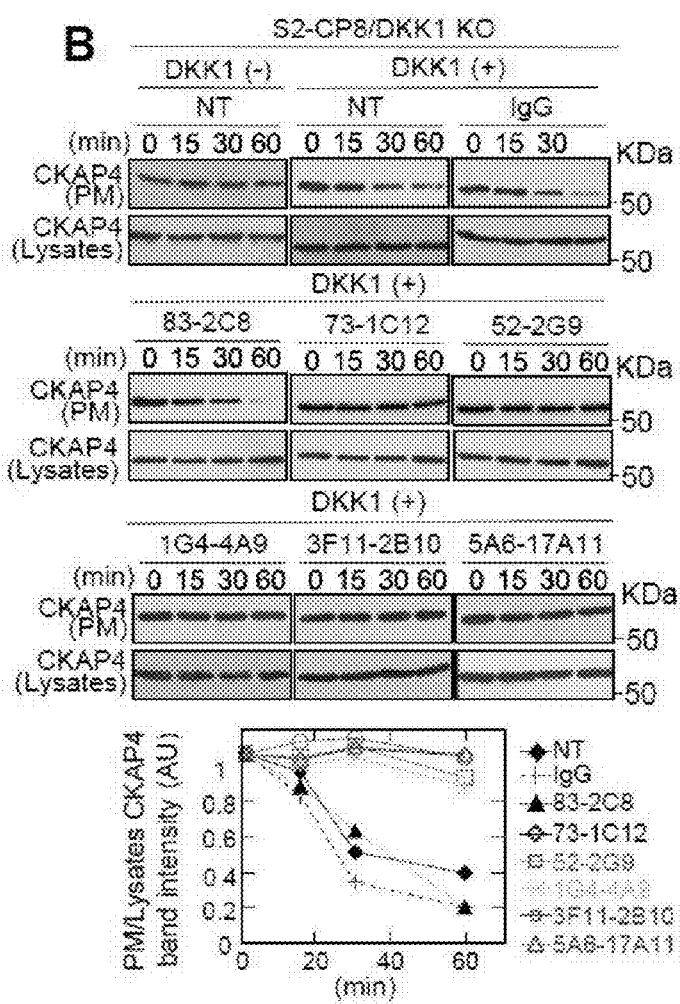

S2-CP8 cells with DKK1 knocked out (S2-CP8/DKK1 KO cells) were prepared. To S2-CP8/DKK1 KO cells, 3 μg/mL of an anti-CKAP4 monoclonal antibody, control IgG (manufactured by FUJIFILM Wako Pure Chemical Corporation, normal mouse IgG, code No. 140-09511) or DKK1-FLAG (a fusion protein in which FLAG tag is added to human DKK1) was added and the S2-CP8/DKK1 KO cells was cultured for one hour. The protein of the cell membrane (PM) of the cultured cells was biotinylated and precipitated using NeutrAvidin beads. CKAP4 in the obtained precipitate (PM) and cell lysates was detected using an anti-CKAP4 polyclonal antibody. The results are shown in FIG. 8A. The results confirmed that antibodies 83-2C8, 73-1C12, 52-2G9, 1G4-4A9, 3F11-2B10, and 5A6-17A11 do not induce the internalization of CKAP4 in S2-CP8/DKK1 KO cells.

To the S2-CP8/DKK1 KO cells, 3 μg/mL of an anti-CKAP4 monoclonal antibody or control IgG was added, the S2-CP8/DKK1 KO cells was cultured for one hour, then 4 nM of DKK1-FLAG was added, and the S2-CP8/DKK1 KO cells were cultured 15, 30, and 60 minutes. The protein of the cell membrane (PM) of the cultured cells was biotinylated and precipitated using NeutrAvidin beads. CKAP4 in the obtained precipitate (IP) and cell lysates was detected using an anti-CKAP4 polyclonal antibody. The results are shown in FIG. 8B. The results confirmed that antibodies 52-2G9, 73-1C12, 1G4-4A9, 3F11-2B10, and 5A6-17A11 inhibited the internalization of CKAP4 in the presence of DKK1, and antibody 83-2C8 did not inhibit the internalization.

8. Evaluation of Immunoprecipitation Capability

The lysate (Input) of S2-CP8 cells (purchased from Cell Resource Center for Biomedical Research, Institute of Development, Aging and Cancer, Tohoku University) was immunoprecipitated using 1 μg/mL of an anti-CKAP4 monoclonal antibody or control IgG (manufactured by FUJIFILM Wako Pure Chemical Corporation, normal mouse IgG 140-09511). CKAP4 in the immunoprecipitate (IP) was detected using an anti-CKAP4 polyclonal antibody. The results are shown in FIG. 7B. The results confirmed that antibodies 73-1C12, 52-2G9, 1G4-4A9, 3F11-2B10, and 5A6-17A11 more efficiently immunoprecipitated the endogenous CKAP4 in S2-CP8 cells than antibody 83-2C8, and in particular, antibodies 1G4-4A9, 3F11-2B10, and 5A6-17A11 have a high effect of immunoprecipitating the endogenous CKAP4 in S2-CP8 cells.

9. Evaluation of Inhibition Capability of AKT Activity

S2-CP8 cells were cultured for one hour in the presence of 50 μg/mL of an anti-CKAP4 monoclonal antibody or control IgG (manufactured by FUJIFILM Wako Pure Chemical Corporation, normal mouse IgG 140-09511). Then, the cells were collected to produce cell lysate, and pAKT, AKT, and clathrin in the lysate were detected using anti-pAKT (phosphorylated AKT) antibody, anti-AKT antibody, and anti-clathrin antibody. The results are shown in FIG. 7C. The results confirmed that the antibodies 73-1C12, 52-2G9, 1G4-4A9, 3F11-2B10, and 5A6-17A11 suppressed the activation of AKT in S2-CP8 cells. Antibody 83-2C8 did not exhibit the inhibition capability of the activation of AKT.

10. Evaluation of Inhibition Capability of Proliferation of Cancer Cells

In the presence of 20 μg/mL of an anti-CKAP4 monoclonal antibody or control IgG (manufactured by FUJIFILM Wako Pure Chemical Corporation, normal mouse IgG, code No. 140-09511), S2-CP8 cells ($1 \times 10^4$ cells) were three-dimensionally cultured on Matrigel for five days, and the total area of cell aggregates per visual field was measured with a 10× objective. The results are shown in FIG. 7D. In FIG. 7D, the left figures are photographs of observation of the state of S2-CP8 cells after culturing for five days, and the right figure is the result (5 visual fields, Mean±s.d.; * means P<0.05,  means P<0.01 (Student's t test) of calculation of the relative value of the total area of the cell aggregates per visual field under each condition when the total area of the cell aggregates per visual field under the condition without addition of an antibody is 1. The results confirmed in FIG. 7A** that though the antibody 83-2C8, which has low inhibition capability of the binding between the extracellular domain of CKAP4 and DKK1, failed to suppress the formation of cell aggregate, antibodies having the high inhibition capability of the binding significantly suppressed the formation of cell aggregate. That is, it was proved that antibodies 73-1C12, 52-2G9, 1G4-4A9, 3F11-2B10, and 5A6-17A11 can suppress the cell proliferation potential of S2-CP8 cells in vitro. Antibody 83-2C8 did not exhibit the inhibition capability for the cell proliferation potential of S2-CP8 cells in vitro.

11. Evaluation of Inhibition Capability of Migration of Cancer Cell

To confirm the influence of anti-CKAP4 antibody on migration capability of cancer cells, A transwell assay was performed using modified Boyden chamber (tissue culture treated, 6.5 mm in diameter, 10-μm thick, 8-am pores; Transwell, Costar, Cambridge, MA). Specifically, the lower surface of the filter was coated with 10 μg/mL of type I collagen for two hours. Then, S2-CP8 cells were suspended in the serum-free DMEM medium containing 0.1% of bovine serum albumin (BSA) and 20 μg/mL of an anti-CKAP4 monoclonal antibody or control IgG (manufactured by FUJIFILM Wako Pure Chemical Corporation, normal mouse IgG, code No. 140-09511) to $1 \times 10^5$ cells/mL, and 200 μL of this cell suspension was added to the upper chamber. A serum-free medium having the same composition as above was added to the lower chamber. The upper chamber was set on the lower chamber and they were incubated at 37° C. for three hours. Then, the cells that migrated to the lower chamber were fixed with PBS containing 4% (w/v) of paraformaldehyde, and the cells were stained with a DNA staining reagent (DRAQ5 DNA dye) to count the number of the cells. The results are shown in FIG. 7E. In FIG. 7E, the left figures are photographs of observation of the cells that migrated to the lower chamber, and the right figure is the result (n=3, Mean±s.d.; ** means P<0.01 (Student's t test)) of calculation of the relative value of the cell number that migrated to the lower chamber under each condition when the number of cells that migrated to the lower chamber under the condition without addition of an antibody is 1. The results confirmed that the antibodies 73-1C12, 52-2G9, 1G4-4A9, 3F11-2B10 and 5A6-17A11 significantly suppress the migration of S2-CP8 cells. Antibody 83-2C8 did not exhibit the inhibition capability for the migration capability of S2-CP8 cells.

12. Evaluation of Neutralizing Activity on In Vivo Tumor Development of Pancreatic Cancer Cells (1)

Into the back of 6-week-old immunodeficient nude mice (male, BALB/cAnNCrj-nu), S2-CP8 cells ($3 \times 10^3$ cells) were subcutaneously injected under anesthesia. When the average tumor size reached 100 mm$^3$, nude mice were randomly divided into seven groups. An anti-CKAP4 monoclonal antibody (73-1C12 (n=6), 52-2G9 (n=4), 1G4-4A9 (n=9), 3F11-2B10 (n=6), 5A6-17A11 (n=5), 83-2C8 (n=3)) or control IgG (manufactured by FUJIFILM Wako Pure Chemical Corporation, normal mouse IgG, code No. 140-09511) (n=8) was intraperitoneally administered twice a week for three weeks (at days 0, 3, 7, 10, 15, 17). The dosage per administration was set to 1 mg/body for antibodies 52-2G9 and 83-2C8, and 200 μg/body for the others. Twenty-one days after the start of administration of the antibody, xenogeneic tumor tissue pieces at the transplantation site of nude mice were analyzed.

Figure 9:
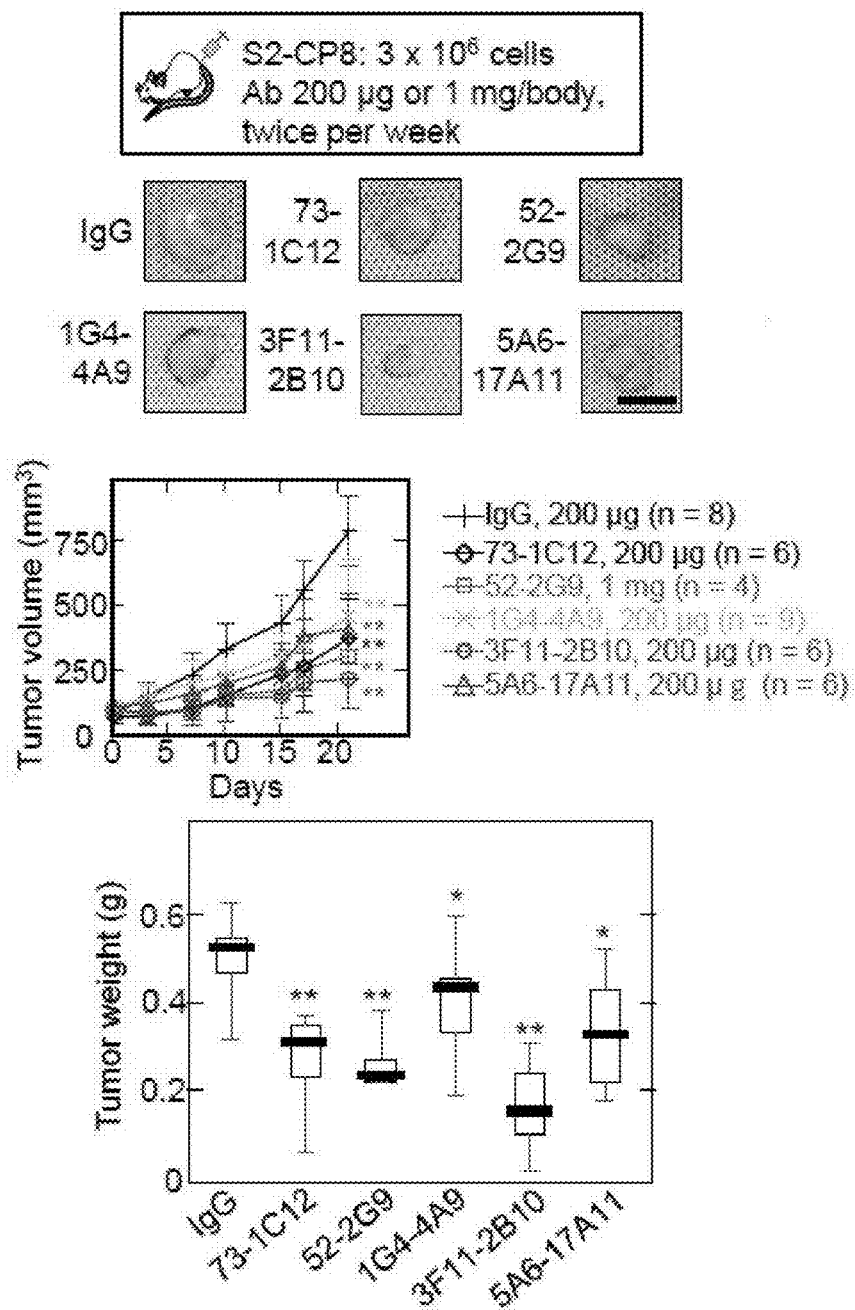
FIG. 9 shows a figure showing the results of appearance observation and measurement of volume and weight of xenogeneic tumor tissue pieces after administering antibodies 73-1C12, 52-2G9, 1G4-4A9, 3F11-2B10, 5A6-17A11, or control IgG to a nude mouse subcutaneously injected with S2-CP8 cells.
Figure 10:
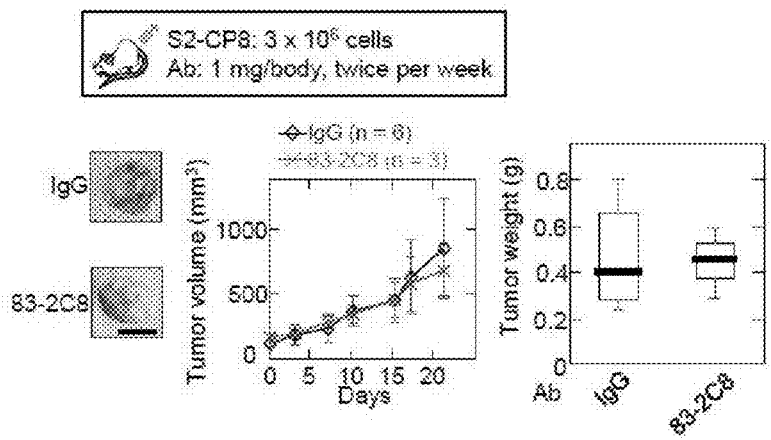
FIG. 10 shows a figure showing the results of appearance observation and measurement of volume and weight of xenogeneic tumor tissue pieces after administering antibody 83-2C8 or control IgG to a nude mouse subcutaneously injected with S2-CP8 cells.

The results are shown in FIGS. 9 and 10. In FIG. 9, the upper figure shows the result of observation of the extirpated xenogeneic tumor tissue pieces, the middle figure shows the result of measurement of the volume of the xenogeneic tumor tissue pieces, and the lower figure shows the result of measurement of the weight of the xenogeneic tumor tissue pieces. In FIG. 10, the left figure shows the result of observation of the extirpated xenogeneic tumor tissue pieces, the middle figure shows the result of measurement of the volume of the xenogeneic tumor tissue pieces, and the right figure shows the result of measurement of the weight of the xenogeneic tumor tissue pieces. Antibody 83-2C8 failed to inhibit the tumor development by S2-CP8 cells. Meanwhile, antibodies 73-1C12, 3F11-2B10, 52-2G9, 1G4-4A9, and 5A6-17A11 inhibited the tumor development by S2-CP8 cells, and in particular, antibody 3F11-2B10 had a high effect.

13. Evaluation of Neutralizing Activity on Tumor Development of Pancreatic Cancer Cells (2)

Into the back of 6-week-old immunodeficient nude mice (male, BALB/cAnNCrj-nu), S2-CP8 cells ($3 \times 10^6$ cells) were subcutaneously injected under anesthesia. When the average tumor size reached 100 mm$^3$, nude mice were randomly divided into two groups. An anti-CKAP4 monoclonal antibody (3F11-2B10 (n=3)) or control IgG (manufactured by FUJIFILM Wako Pure Chemical Corporation, normal mouse IgG, code No. 140-09511) (n=3) was intraperitoneally injected twice a week for three weeks (at days 0, 3, 7, 10, 15, 17) at 50 μg/body. Twenty-one days after the start of administration of the antibody, xenogeneic tumor tissue pieces at the transplantation site of nude mice were analyzed.

Figure 11:
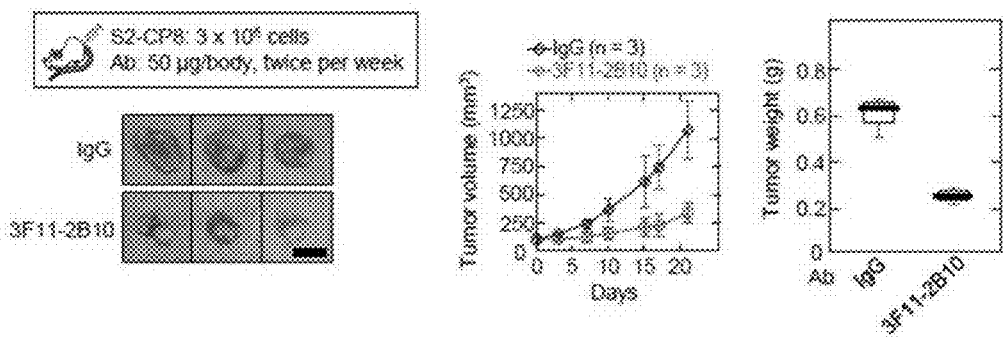
FIG. 11 shows a figure showing the results of appearance observation and measurement of volume and weight of xenogeneic tumor tissue pieces after administering antibody 3F11-2B10 or control IgG to a nude mouse subcutaneously injected with S2-CP8 cells at a lower dose than that in FIG. 9.

The results are shown in FIG. 11. In FIG. 11, the left figure shows the result of observation of the extirpated xenogeneic tumor tissue pieces, the middle figure shows the result of measurement of the volume of the xenogeneic tumor tissue pieces, and the right figure shows the result of measurement of the weight of the xenogeneic tumor tissue pieces. The results proved that antibody 3F11-2B10 can inhibit tumor development by S2-CP8 cells even at a low dose.

14. Evaluation of Neutralizing Activity on Tumor Development of Pancreatic Cancer Cells (3)

Into the back of 6-week-old immunodeficient nude mice (male, BALB/cAnNCrj-nu), S2-CP8 cells ($3 \times 10^6$ cells) were subcutaneously injected under anesthesia. When the average tumor size reached 100 mm$^3$, nude mice were randomly divided into four groups. An anti-CKAP4 monoclonal antibody (3F11-2B10) (25, 50, or 200 μg/body) or control IgG (manufactured by FUJIFILM Wako Pure Chemical Corporation, normal mouse IgG, code No. 140-09511) (200 μg/body) was intraperitoneally injected twice a week for three weeks (at days 0, 3, 7, 10, 15, 17). Twenty-one days after the start of administration of the antibody, the volume and weight of the xenogeneic tumor tissue pieces were measured.

Figure 12:
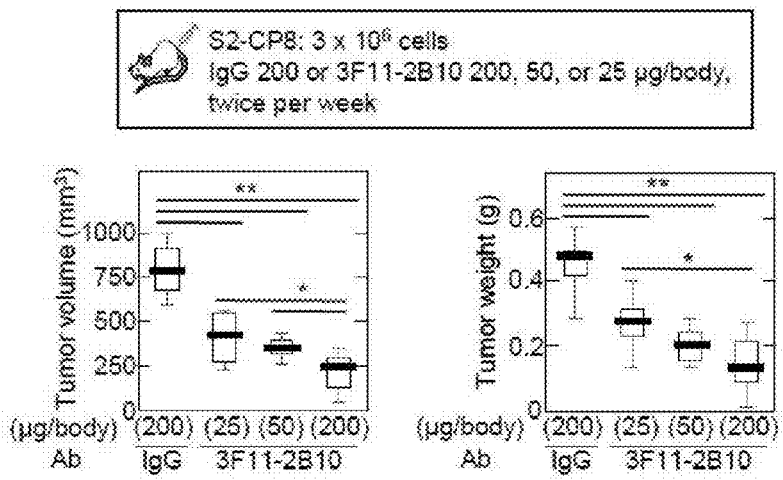
FIG. 12 shows a figure showing the results of measurement of volume and weight of xenogeneic tumor tissue pieces after administering antibody 3F11-2B10 or control IgG to a nude mouse subcutaneously injected with S2-CP8 cells.

The results are shown in FIG. 12. The results also confirmed that tumor development by S2-CP8 cells can be inhibited even when the dosage of antibody 3F11-2B10 is reduced to 25 μg/body or 50 μg/body.

15. Evaluation of Neutralizing Activity on Tumor Development of Pancreatic Cancer Cells (4)

Into the back of 6-week-old immunodeficient nude mice (male, BALB/cAnNCrj-nu), S2-CP8 cells ($3 \times 10^6$ cells) were subcutaneously injected under anesthesia. When the average tumor size reached 100 mm$^3$, nude mice were randomly divided into six groups shown in Table 1 below, and each administration sample was intraperitoneally injected twice a week for three weeks (at days 0, 3, 7, 10, 15, 17). Twenty-one days after the start of administration of the administration sample, xenogeneic tumor tissue pieces at the transplantation site of nude mice were analyzed.

TABLE 1

| Group | Administration sample/Dose |
|---|---|
| IgG, 50 μg (IgG(50)) | Control IgG (manufactured by FUJIFILM Wako Pure Chemical Corporation, normal mouse IgG, code No. 140-09511) was administered at 50 μg/body per administration (n = 6) |
| GEM, 400 μg (GEM(400)) | Gemcitabine (manufactured by FUJIFILM Wako Pure Chemical Corporation) was administered at 400 μg/body per administration (n = 6) |
| GEM, 1000 μg (GEM(1000)) | Gemcitabine (manufactured by FUJIFILM Wako Pure Chemical Corporation, normal mouse IgG, code No. 140-09511) was administered at 1000 μg/body per administration (n = 6) |
| 3F11-2B10, 50 μg (3F(50)) | Antibody 3F11-2B10 was administered at 50 μg/body per administration (n = 6) |
| 3F11-2B10, 50 μg + GEM, 400 μg (3F(50) + GEM(400)) | Antibody 3F11-2B10 was administered at 50 μg/body per administration, and gemcitabine (manufactured by FUJIFILM Wako Pure Chemical Corporation) was administered at 400 μg/body per administration (n = 6) |

TABLE 1-continued

| Group | Administration sample/Dose |
|---|---|
| 3F11-2B10, 50 μg + GEM, 1000 μg (3F(50) + GEM(1000)) | Antibody 3F11-2B10 was administered at 50 μg/body per administration, and gemcitabine (manufactured by FUJIFILM Wako Pure Chemical Corporation) was administered at 1000 μg/body per administration (n = 6) |

Figure 13:
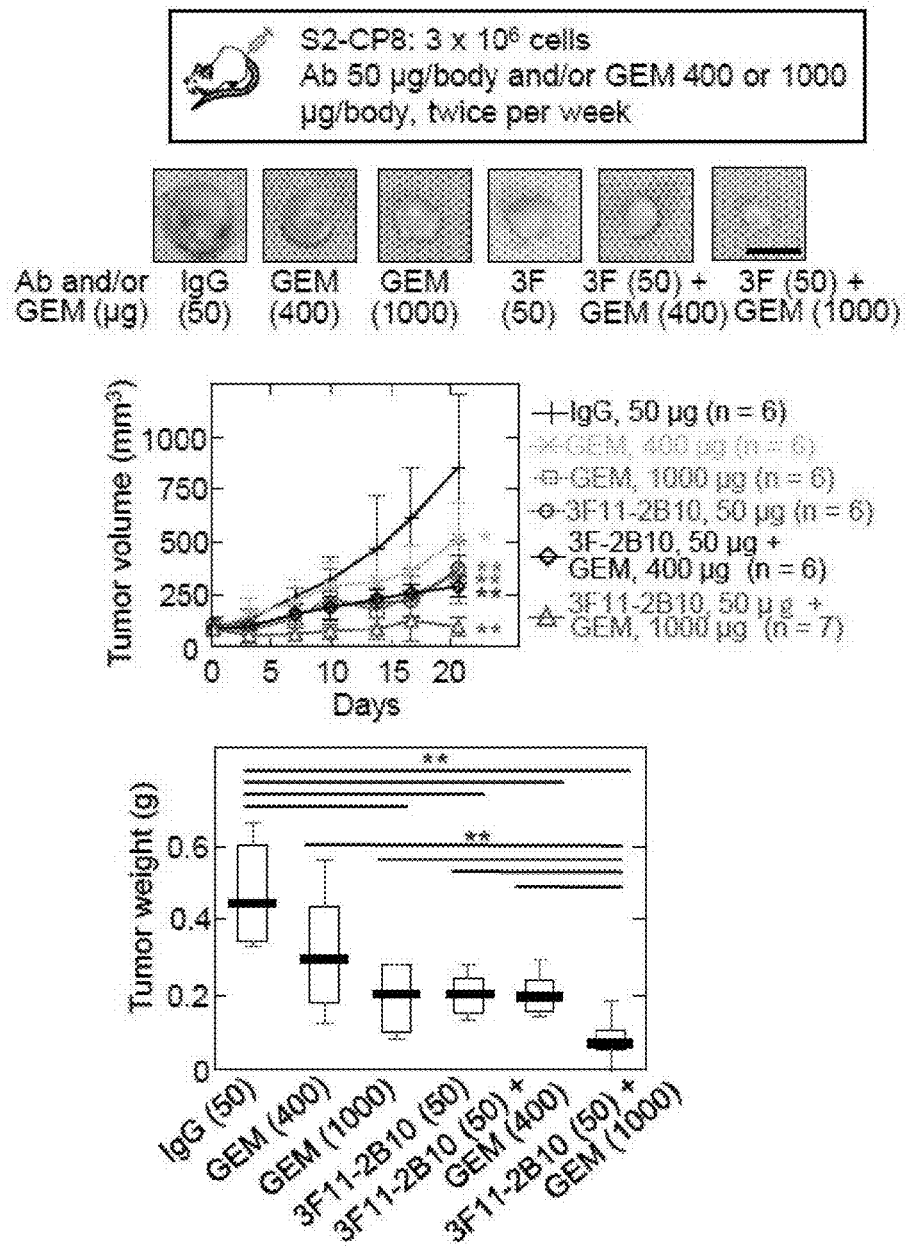
FIG. 13 shows a figure showing the results of appearance observation and measurement of volume and weight of xenogeneic tumor tissue pieces after administering antibody 3F11-2B10 and/or gemcitabine, or control IgG to a nude mouse subcutaneously injected with S2-CP8 cells.

The results are shown in FIG. 13. In FIG. 13, the upper figure shows the result of observation of the extirpated xenogeneic tumor tissue pieces, the middle figure shows the result of measurement of the volume of the xenogeneic tumor tissue pieces, and the lower figure shows the result of measurement of the weight of the xenogeneic tumor tissue pieces. Though the combined administration of 50 μg/body of antibody 3F11-2B10 and 400 μg/body of gemcitabine had an antitumor effect similar to that of the single administration of 50 μg/body of antibody 3F11-2B10, the combined administration of 50 μg/body of antibody 3F11-2B10 and 1000 μg/body of gemcitabine exhibited the excellent antitumor effect.

16. Evaluation of Prognosis Extending Capability for Peritoneal Metastasis Model of Pancreatic Cancer Cells Into 6-week-old immunodeficient nude mice (male, BALB/cAnNCrj-nu), S2-CP8 cells ($3 \times 10^6$ cells) were intraperitoneally injected under anesthesia. Two days after the injection of S2-CP8 cells, nude mice were randomly divided into three groups, an anti-CKAP4 monoclonal antibody (3F11-2B10) (n=10) or control IgG (manufactured by FUJIFILM Wako Pure Chemical Corporation, normal mouse IgG, code No. 140-09511) (n=10) was intraperitoneally administered twice a week at 50 μg/body, and the number of days of survival of nude mice was measured. It has been confirmed that the immunodeficient nude mice into which S2-CP8 cells were intraperitoneally injected develop peritoneal metastasis, and can be used as peritoneal metastasis models.

Figure 14:
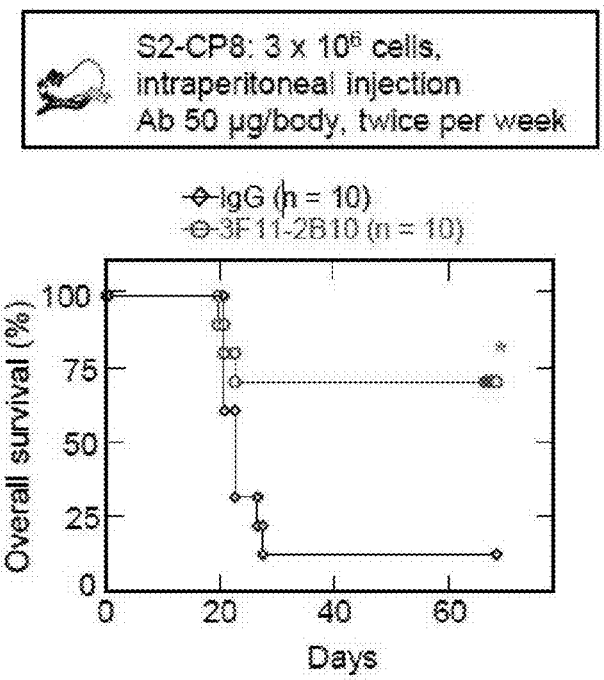
FIG. 14 is a figure showing the results of measurement of the number of days of survival after administering antibody 3F11-2B10 or control IgG to a nude mouse intraperitoneally injected with S2-CP8 cells.

The results are shown in FIG. 14. The results proved that antibodies 3F11-2B10 and 52-2G9 have prognosis extending capability for peritoneal metastasis of S2-CP8 cells.

17. Evaluation of Neutralizing Activity on Tumor Development of Pancreatic Cancer Cells (5)

Into the back of 6-week-old immunodeficient nude mice (male, BALB/cAnNCrj-nu), HPAF-II cells ($3 \times 10^6$ cells) were subcutaneously injected under anesthesia. When the average tumor size reached 100 mm$^3$, nude mice were randomly divided into two groups. An anti-CKAP4 monoclonal antibody (3F11-2B10 (n=6)) or control IgG (manufactured by FUJIFILM Wako Pure Chemical Corporation, normal mouse IgG, code No. 140-09511) (n=7) was intraperitoneally injected twice a week for three weeks (at days 0, 3, 7, 10, 15, 17) at 200 μg/body. Twenty-one days after the start of administration of the antibody, xenogeneic tumor tissue pieces at the transplantation site of nude mice were analyzed.

Figure 15:
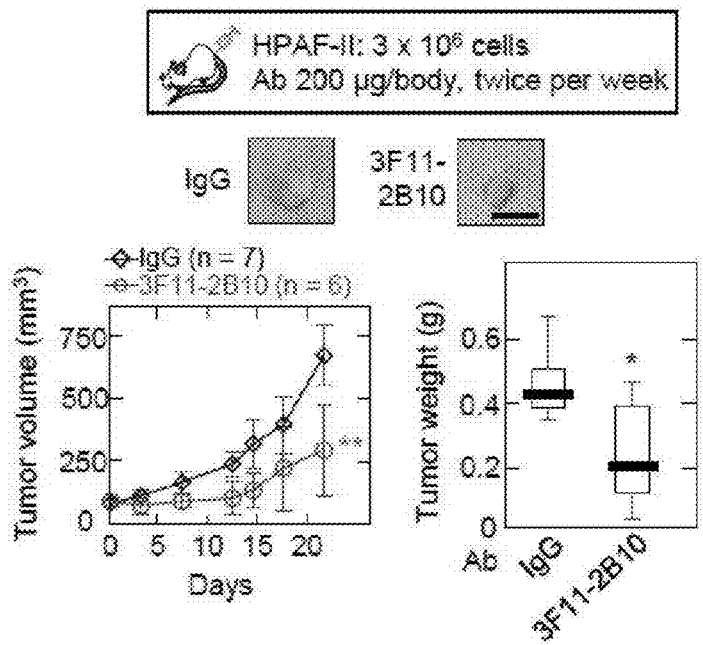
FIG. 15 shows a figure showing the results of appearance observation and measurement of volume and weight of xenogeneic tumor tissue pieces after administering antibody 3F11-2B10 to a nude mouse subcutaneously injected with human pancreatic cancer cells (HPAF-II cells).

The results are shown in FIG. 15. In FIG. 15, the upper figure shows the result of observation of the extirpated xenogeneic tumor tissue pieces, the lower left figure shows the result of measurement of the volume of the xenogeneic tumor tissue pieces, and the lower right figure shows the result of measurement of the weight of the xenogeneic tumor tissue pieces. The results confirmed that antibody 3F11-2B10 has inhibitory action on tumor development by HPAF-II cells.

18. Evaluation of Neutralizing Activity on Tumor Development of Lung Cancer Cells Into the back of 6-week-old immunodeficient nude mice (male, BALB/cAnNCrj-nu), human alveolar basal epithelial adenocarcinoma cells (A549 cells) ($5 \times 10^6$ cells) were subcutaneously injected under anesthesia. When the average tumor size reached 100 mm$^3$, nude mice were randomly divided into three groups. An anti-CKAP4 monoclonal antibody (73-1C12 (n=6) and 3F11-2B (n=6)) or control IgG (manufactured by FUJIFILM Wako Pure Chemical Corporation, normal mouse IgG, code No. 140-09511) (n=6) was intraperitoneally administered twice a week for four weeks (at days 0, 3, 8, 10, 14, 17, 21, 24) at 200 μg/body. The dosage per administration was set to 200 μg/body for antibody 73-1C12 and control IgG, and 50 μg/body for antibody 3F11-2B. Twenty-eight days after the start of administration of the antibody, xenogeneic tumor tissue pieces at the transplantation site of nude mice were analyzed.

Figure 16:
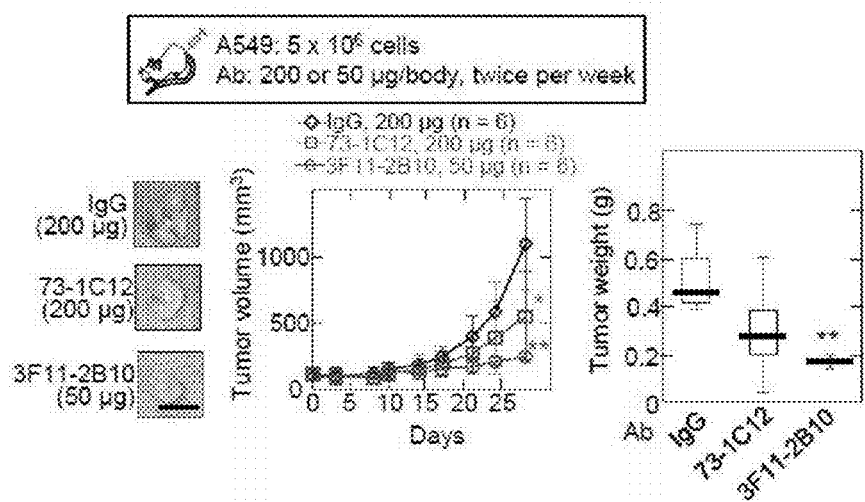
FIG. 16 shows a figure showing the results of appearance observation and measurement of volume and weight of xenogeneic tumor tissue pieces after administering antibodies 3F11-2B, 73-1C12, or control IgG to a nude mouse subcutaneously injected with human lung cancer cells (A549 cells).

The results are shown in FIG. 16. In FIG. 16, the left figure shows the result of observation of the extirpated xenogeneic tumor tissue pieces, the middle figure shows the result of measurement of the volume of the xenogeneic tumor tissue pieces, and the right figure shows the result of measurement of the weight of the xenogeneic tumor tissue pieces. The results confirmed that antibodies 3F11-2B and 73-1C12 have inhibitory action on tumor development by A549 cells. In particular, antibody 3F11-2B exhibited excellent antitumor effect.

19. Measurement of CKAP4 by Sandwich ELISA (1)

(Preparation of Sample Solution)

A sample solution obtained by diluting stepwise recombinant human CKAP4 was prepared.

(Measurement by Sandwich ELISA)

To each well of a 96-well plate (9018, Corning), 100 μL of 1 μg/mL of an anti-CKAP4 monoclonal antibody (3F11-2B10) solution was added, and incubated overnight at room temperature. Then, after washing with PBS containing 0.05% Tween 20, blocking solution (PBS containing 1% BSA) was added to each well and the well was incubated at room temperature for one hour. Then, the well was washed with PBS containing 0.05% Tween 20, 50 μL of a sample solution was added to each well, and the well was incubated at room temperature for two hours. After washing, 50 μL of 2 μg/mL of a biotin-labeled anti-CKAP4 monoclonal antibody (1G4-4A9) solution was added, and the mixture was incubated at room temperature for one hour. After washing, 50 μL of HRP (horseradish peroxidas)-streptavidin (DY998, R & D Systems, Inc., Minneapolis, MN) solution was added to each well and the well was incubated at room temperature for 20 minutes. Then, a substrate solution (DY999, R & D Systems, Inc., Minneapolis, MN) was added to each well and allowed to react for 10 minutes. The reaction was stopped by adding 50 μL of a reaction stop solution (Cell Signaling Technology, Beverly, MA) to each well, and absorbances at wavelengths of 450 nm and 540 nm were measured with a microplate reader.
(Result)

Figure 17:
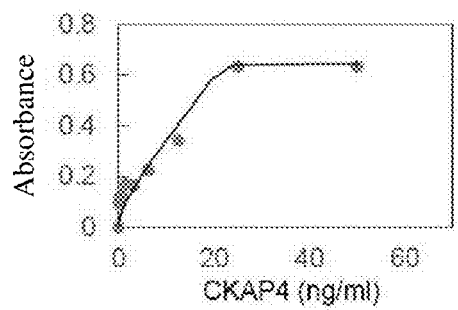
FIG. 17 is a figure showing the results of measurement of the CKAP4 concentration in a solution in which recombinant human CKAP4 is diluted stepwise determined by sandwich ELISA using antibody 3F11-2B10 as a capture antibody and antibody 1G4-4A9 as a detection antibody.

The results are shown in FIG. 17. A value obtained by subtracting the absorbance at 540 nm from the absorbance at a wavelength of 450 nm is shown in the longitudinal axis in FIG. 17. The results confirmed that 1 ng/mL or more of CKAP4 can be quantified by sandwich ELISA using antibody 3F11-2B10 as a capture antibody and antibody 1G4-4A9 as a detection antibody.

20. Measurement of CKAP4 by Sandwich ELISA (2)

Samples shown in Table 2 were prepared, and sandwich ELISA was performed in the same manner as in "19. Measurement of CKAP4 by sandwich ELISA (1)" to measure CKAP4. The serum samples shown in Table 2 were prepared by collecting blood with an anticoagulant-free vacuum blood collection tube and centrifuging it. The plasma samples shown in Table 2 were prepared by collecting blood with an EDTA-added vacuum blood collection tube and centrifuging it. Serum samples and plasma samples were stored at −80° C. until use, and were used for the test immediately after thawing. All samples were diluted with PBS containing 1% BSA. Sample C shown in Table 2 is a case without a history of treatment for cancer at the time of blood collection.

TABLE 2

| Sample | Derivation/Preparation method |
|---|---|
| A1 | Sample of plasma from healthy subject A |
| A2 | Sample of plasma from healthy subject A with recombinant human CKAP4 added at an amount of 25 ng/mL |
| A3 | Sample of serum from healthy subject A |
| A4 | Sample of serum from healthy subject A with recombinant human CKAP4 added at an amount of 25 ng/mL |
| B1 | Sample of plasma from healthy subject B |
| B2 | Sample obtained by diluting plasma from healthy subject B twice |
| B3 | Sample of plasma from healthy subject B with recombinant human CKAP4 added at an amount of 20 ng/mL |
| B4 | Sample obtained by diluting plasma from healthy subject B twice, and then adding recombinant human CKAP4 at an amount of 20 ng/mL |
| B5 | Sample of serum from healthy subject B |
| B6 | Sample of serum from healthy subject B with recombinant human CKAP4 added at an amount of 20 ng/mL |
| C | Serum from patient with esophageal squamous cell carcinoma |

Figure 18:
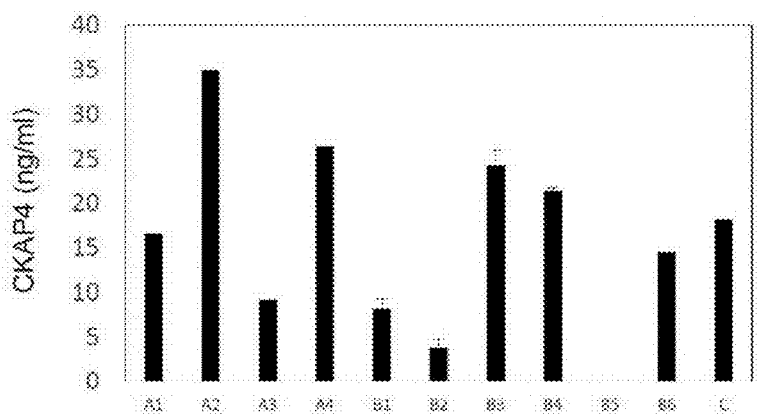
FIG. 18 is a figure showing the CKAP4 concentration in various sample solutions determined by sandwich ELISA using antibody 3F11-2B10 as a capture antibody and antibody 1G4-4A9 as a detection antibody. Details of the samples are shown in Table 2.

The results are shown in FIG. 18. The results also confirmed that CKAP4 can be quantified by sandwich ELISA using antibody 3F11-2B10 as a capture antibody and antibody 1G4-4A9 as a detection antibody.

21. Measurement of CKAP4 in Serum Exosomes by Exosome ELISA (Measurement by PS Capture™ Exosome ELISA Kit)

Samples shown in Table 3 were prepared, and CKAP4 in exosomes contained in the samples was measured using PS Capture™ Exosome ELISA Kit. After washing each well of Exosome Capture 96 Well Plate, an accessory of the Kit, with the reaction/washing solution, 100 μL of the sample solution was added, and the well was incubated at room temperature for two hours. After washing, 100 μL of 6.25 ng/mL of a biotin-labeled anti-CKAP4 monoclonal antibody (5A6-17A11) solution was added, and the mixture was incubated at room temperature for one hour. After washing, 100 μL of Poly-HRP Streptavidin reaction liquid was added to each well, and the well was incubated at room temperature for one hour. After washing, a substrate solution was added to each well, and the mixture was allowed to react for 30 minutes. To each well, 100 μL of a reaction stop solution was added to stop the reaction, and absorbances at wavelengths of 450 nm and 620 nm were measured with a microplate reader. Things used other than the anti-CKAP4 monoclonal antibody were accessories of the Kit.

TABLE 3

| Sample | Derivation/Preparation method/Measuring condition |
|---|---|
| S1 | Sample obtained by concentrating 50 ml of conditioned medium of S2-CP8 cells with CKAP4 knocked out 50 times Antibody 5A6-17A11 was added |
| S2 | Sample obtained by concentrating 50 ml of conditioned medium of S2-CP8 cells that overexpress CKAP4 50 times Antibody 5A6-17A11 was added |
| B7 | Sample obtained by diluting 10 μl of plasma from healthy subject B 10 times Antibody 5A6-17A11 was not added |
| B8 | Sample obtained by diluting 1 μl of plasma from healthy subject B 100 times Antibody 5A6-17A11 was added |

Figure 19:
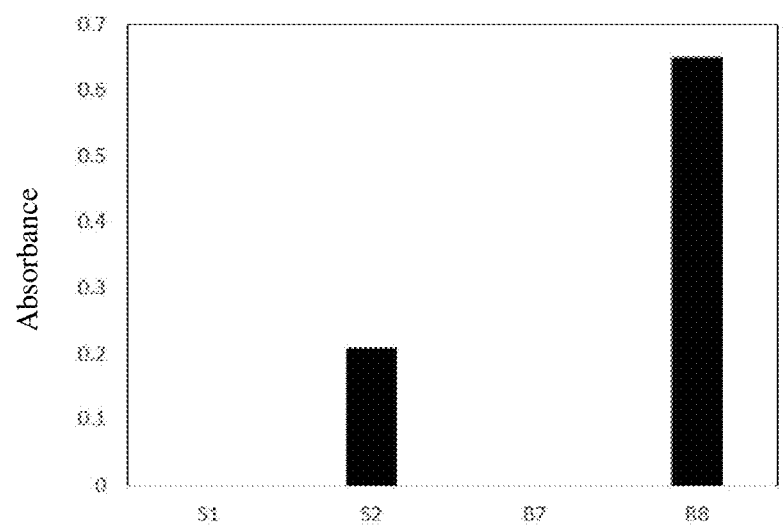
FIG. 19 is a figure showing the results of detection of CKAP4 in exosomes in samples by exosome ELISA with PS Capture™ Exosome ELISA Kit using antibody 5A6-17A11 as a detection antibody. Details of the samples are shown in Table 3.

The results are shown in FIG. 19. A value obtained by subtracting the absorbance at 620 nm from the absorbance at a wavelength of 450 nm is shown in the longitudinal axis in FIG. 19. The results confirmed that by using antibody 5A6-17A11 as a detection antibody, CKAP4 in exosomes contained in the sample can be detected using PS Capture™ Exosome ELISA Kit.

22. Measurement of CKAP4 in Serum of Patient with Human Pancreatic Ductal Adenocarcinoma
(Sample Preparation)

The serum obtained from a patient with human pancreatic ductal adenocarcinoma (47 cases) and a diluted solution obtained by diluting the serum 10 times were prepared as a sample solution.
(Measurement of CKAP4 in Serum by Sandwich ELISA)

CKAP4 in the serum in a patient with human pancreatic ductal adenocarcinoma was measured by the following method by sandwich ELISA. To each well of a 96-well plate (9018, Corning), 100 μL of 2 μg/mL of an anti-CKAP4 monoclonal antibody (3F11-2B10) solution was added, and the well was incubated overnight at room temperature. Then, after washing with PBS containing 0.05% Tween 20, blocking solution (PBS containing 1% BSA) was added to each well and the well was incubated at room temperature for one hour. Then, the well was washed with PBS containing 0.05% Tween 20, 50 μL of the sample solutions (the serum and the 10-fold diluted solution) were added to each well, and the well was incubated at room temperature for two hours. After washing, 100 μL of 1 μg/mL of a biotin-labeled anti-CKAP4 monoclonal antibody (1G4-4A9) solution was added, and the mixture was incubated at room temperature for one hour. After washing, 50 μL of HRP (horseradish peroxidas)-streptavidin (DY998, R & D Systems, Inc., Minneapolis, MN) solution was added to each well and the well was incubated at room temperature for 20 minutes. Then, a substrate solution (DY999, R & D Systems, Inc., Minneapolis, MN) was added to each well and allowed to react for 10 minutes. The reaction was stopped by adding 50 μL of a reaction stop solution (Cell Signaling Technology, Beverly, MA) to each well, and absorbances at wavelengths of 450 nm and 540 nm were measured with a microplate reader.

Measurement in the same manner was performed using a solution obtained by diluting recombinant human CKAP4 stepwise to prepare a standard curve. When the concentration of CKAP4 was less than 1 ng/mL (the lower limit value of the standard curve), the concentration was taken as 0 ng/mL.

(Measurement of CKAP4 in Serum Exosomes by Exosome ELISA)

CKAP4 in exosomes contained in a serum was measured using PS Capture™ Exosome ELISA Kit by the following method. After washing each well of Exosome Capture 96 Well Plate, an accessory of the Kit, with the reaction/washing solution, 100 μL of the sample solution (a serum) was added, and the well incubated at room temperature for two hours. After washing, 100 μL of 100 ng/mL of a biotin-labeled anti-CKAP4 monoclonal antibody (5A6-17A11) solution was added, and the mixture was incubated at room temperature for one hour. After washing, 100 μL of Poly-HRP Streptavidin reaction liquid was added to each well, and the well was incubated at room temperature for one hour. After washing, a substrate solution was added to each well, and the mixture was allowed to react for 30 minutes. To each well, 100 μL of a reaction stop solution was added to stop the reaction, and absorbances at wavelengths of 450 nm and 620 nm were measured with a microplate reader. Things used other than the anti-CKAP4 monoclonal antibody were accessories of the Kit.

(Result)

Figure 20:
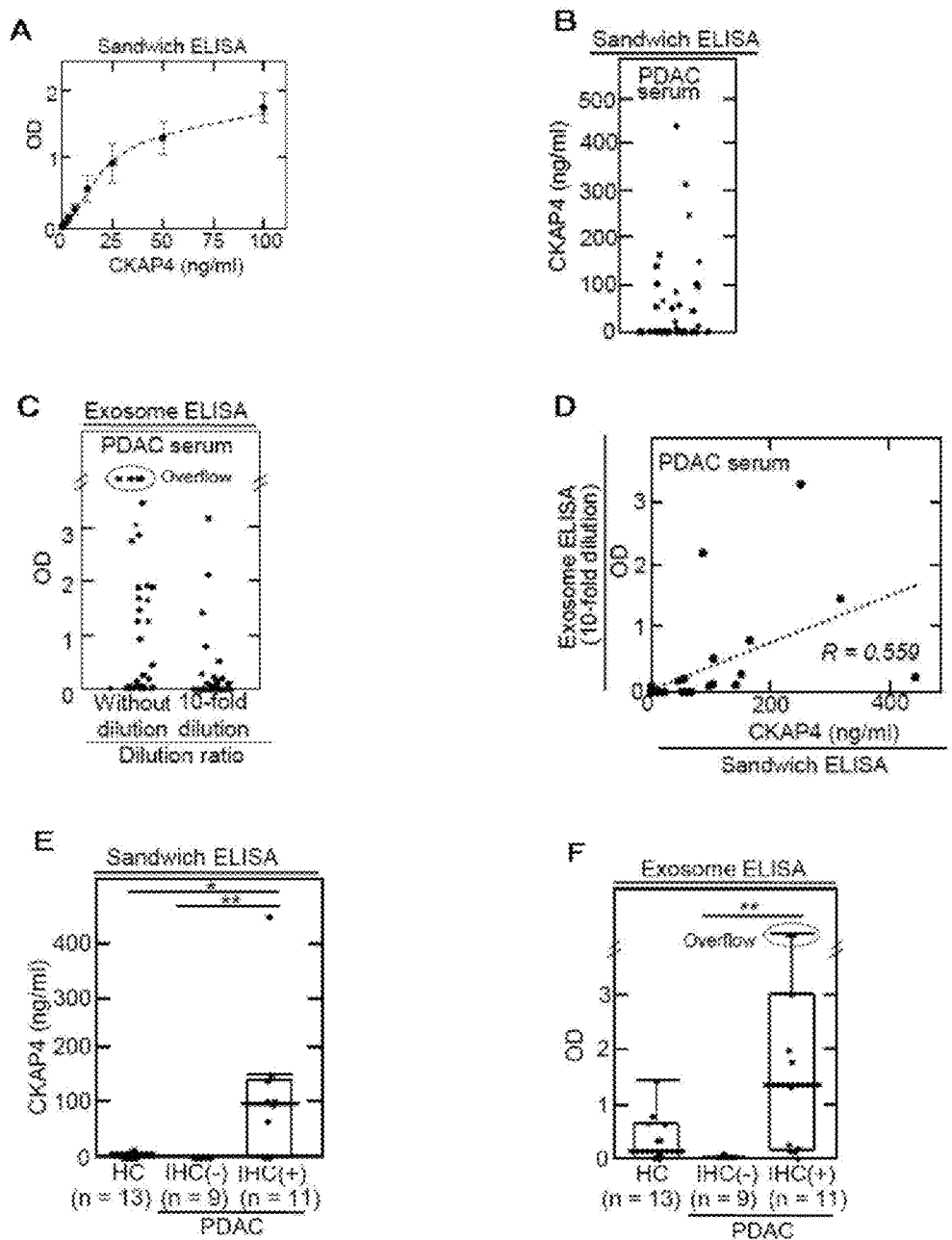
FIG. 20A is a figure showing a standard curve produced using a solution in which recombinant human CKAP4 is diluted stepwise in sandwich ELISA using antibody 3F11-2B10 as a capture antibody and antibody 1G4-4A9 as a detection antibody.
FIG. 20B is a figure showing the results of measurement of the CKAP4 concentration in the serum of a patient with human pancreatic ductal adenocarcinoma by sandwich ELISA using antibody 3F11-2B10 as a capture antibody and antibody 1G4-4A9 as a detection antibody.
FIG. 20C is a figure showing the results of detection of CKAP4 in exosomes contained in the serum of a patient with human pancreatic ductal adenocarcinoma by exosome ELISA using antibody 5A6-17A11 as a detection antibody. The left lane is the data of the sample without dilution, and the right lane is the data of the sample diluted 10-fold.
FIG. 20D is a figure comparing the measurement results of CKAP4 in the serum and the measurement results of CKAP4 in exosomes for each patient.
FIG. 20E is a figure showing the results of measurement of CKAP4 in the sera obtained from healthy subjects (HC), patients with pancreatic ductal adenocarcinoma immunohistochemically confirmed to be CKAP4 negative (PDAC IHC (−)), and patients with pancreatic ductal adenocarcinoma immunohistochemically confirmed to be CKAP4 positive (PDAC IHC (+)) by sandwich ELISA.
FIG. 20F is a figure showing the results of measurement of CKAP4 in exosomes contained in the sera obtained from healthy subjects (HC), patients with pancreatic ductal adenocarcinoma immunohistochemically confirmed to be CKAP4 negative (PDAC IHC (−)), and patients with pancreatic ductal adenocarcinoma immunohistochemically confirmed to be CKAP4 positive (PDAC IHC (+)) by exosome ELISA using antibody 5A6-17A11 as a detection antibody.

A standard curve produced using a solution obtained by diluting recombinant human CKAP4 stepwise is shown in FIG. 20A. A value obtained by subtracting the absorbance at 540 nm from the absorbance at a wavelength of 450 nm is shown in the longitudinal axis in FIG. 20A. As can be seen from FIG. 20A, it was confirmed that CKAP4 in the concentration range of 1 to 25 ng/mL can be quantified by sandwich ELISA under the above-mentioned conditions.

The results of measurement of CKAP4 in the serum of a patient with human pancreatic ductal adenocarcinoma by sandwich ELISA are shown in FIG. 20B. The results confirmed that CKAP4 in the serum of a patient with human pancreatic ductal adenocarcinoma can be measured by sandwich ELISA using antibody 3F11-2B10 as a capture antibody and antibody 1G4-4A9 as a detection antibody.

The results of measurement of CKAP4 in exosomes contained in the serum of a patient with human pancreatic ductal adenocarcinoma by exosome ELISA are shown in FIG. 20C. A value obtained by subtracting the absorbance at 620 nm from the absorbance at a wavelength of 450 nm is shown in the longitudinal axis in FIG. 20C. The results confirmed that by using antibody 5A6-17A11 as a detection antibody, CKAP4 in exosomes contained in the serum of a patient with human pancreatic ductal adenocarcinoma can be detected.

A comparison between the measurement results of CKAP4 in the serum by sandwich ELISA and the measurement results of CKAP4 in serum exosomes by exosome ELISA for each patient is shown in FIG. 20D. The results proved that the concentration of CKAP4 in the serum of a patient with human pancreatic ductal adenocarcinoma correlates with the concentration of CKAP4 in serum exosomes.

23. Measurement of CKAP4 in Sera of Patient with Human Pancreatic Ductal Adenocarcinoma and Healthy Subject (Sample Preparation)

The sera obtained from healthy subjects (HC) (13 cases), patients with pancreatic ductal adenocarcinoma immunohistochemically confirmed to be CKAP4 negative (PDAC IHC (−)) (9 cases), and patients with pancreatic ductal adenocarcinoma immunohistochemically confirmed to be CKAP4 positive (PDAC IHC (+)) (11 cases) were prepared as sample solutions.

(Measurement of CKAP4 in Serum)

The concentration of CKAP4 in a serum was measured according to the method described in the "Measurement of CKAP4 in serum by sandwich ELISA" in "22. Measurement of CKAP4 in serum of patient with human pancreatic ductal adenocarcinoma".

(Measurement of CKAP4 in Exosomes)

The concentration of CKAP4 in serum exosomes was measured according to the method described in the "Measurement of CKAP4 in serum exosomes by exosome ELISA" in "22. Measurement of CKAP4 in serum of patient with human pancreatic ductal adenocarcinoma".

(Result)

The results of measurement of CKAP4 in the serum are shown in FIG. 20E, and the results of measurement of CKAP4 in the serum exosomes are shown in FIG. 20F. A value obtained by subtracting the absorbance at 540 nm from the absorbance at a wavelength of 450 nm is shown in the longitudinal axis in FIG. 20F. The sera from patients with CKAP4-positive pancreatic ductal adenocarcinoma exhibited significantly higher CKAP4 concentrations compared to the sera from CKAP4-negative pancreatic ductal adenocarcinoma patients and healthy subjects. The serum exosomes from patients with CKAP4-positive pancreatic ductal adenocarcinoma exhibited significantly higher CKAP4 concentrations compared to the serum exosomes from CKAP4-negative pancreatic ductal adenocarcinoma patients, and further exhibited a tendency of higher CKAP4 concentrations compared to the exosomes from healthy subjects (p=0.064).

The invention claimed is:

1. An anti-CKAP4 monoclonal antibody or a fragment thereof produced by hybridoma 3F11-2B10, deposited as NITE BP-03885 on Apr. 18, 2023, with the NITE Patent Microorganisms Depositary National Institute of Technology and Evaluation, or a humanized antibody thereof or a fragment thereof.

2. The anti-CKAP4 monoclonal antibody or fragment thereof according to claim 1, having an isotype of IgG.

3. An antitumor drug comprising the anti-CKAP4 monoclonal antibody or fragment thereof according to claim 1 as an active ingredient.

4. A method of treating lung cancer, pancreatic cancer, or esophageal cancer in a subject comprising administering to a subject the antitumor drug according to claim 3.

5. A method for treating a tumor, comprising a step of administering the anti-CKAP4 monoclonal antibody or fragment thereof according to claim 1 to a patient suffering from a tumor.

6. A method for measuring CKAP4, comprising a step of measuring CKAP4 using the anti-CKAP4 monoclonal antibody or fragment thereof according to claim 1.

7. The method for measuring CKAP4 according to claim 6, wherein the anti-CKAP4 monoclonal antibody or fragment thereof is used as at least one of a capture antibody and a detection antibody in ELISA.

* * * * *

SEQUENCE LISTING

```
<160> NUMBER OF SEQ ID NOS: 1

<210> SEQ ID NO 1
<211> LENGTH: 602
<212> TYPE: PRT
<213> ORGANISM: Homo sapiens

<400> SEQUENCE: 1

Met Pro Ser Ala Lys Gln Arg Gly Ser Lys Gly Gly His Gly Ala Ala
1               5                   10                  15

Ser Pro Ser Glu Lys Gly Ala His Pro Ser Gly Gly Ala Asp Asp Val
            20                  25                  30
```

```
Ala Lys Lys Pro Pro Ala Pro Gln Gln Pro Pro Pro Pro Ala
        35              40              45
Pro His Pro Gln Gln His Pro Gln Gln His Pro Gln Asn Gln Ala His
    50              55              60
Gly Lys Gly Gly His Arg Gly Gly Gly Gly Gly Gly Lys Ser Ser
65              70              75              80
Ser Ser Ser Ser Ala Ser Ala Ala Ala Ala Ala Ala Ala Ser Ser
            85              90              95
Ser Ala Ser Cys Ser Arg Arg Leu Gly Arg Ala Leu Asn Phe Leu Phe
            100             105             110
Tyr Leu Ala Leu Val Ala Ala Ala Phe Ser Gly Trp Cys Val His
            115             120             125
His Val Leu Glu Glu Val Gln Gln Val Arg Arg Ser His Gln Asp Phe
    130             135             140
Ser Arg Gln Arg Glu Glu Leu Gly Gln Gly Leu Gln Gly Val Glu Gln
145             150             155             160
Lys Val Gln Ser Leu Gln Ala Thr Phe Gly Thr Phe Glu Ser Ile Leu
                165             170             175
Arg Ser Ser Gln His Lys Gln Asp Leu Thr Glu Lys Ala Val Lys Gln
            180             185             190
Gly Glu Ser Glu Val Ser Arg Ile Ser Glu Val Leu Gln Lys Leu Gln
            195             200             205
Asn Glu Ile Leu Lys Asp Leu Ser Asp Gly Ile His Val Val Lys Asp
    210             215             220
Ala Arg Glu Arg Asp Phe Thr Ser Leu Glu Asn Thr Val Glu Glu Arg
225             230             235             240
Leu Thr Glu Leu Thr Lys Ser Ile Asn Asp Asn Ile Ala Ile Phe Thr
                245             250             255
Glu Val Gln Lys Arg Ser Gln Lys Glu Ile Asn Asp Met Lys Ala Lys
            260             265             270
Val Ala Ser Leu Glu Glu Ser Glu Gly Asn Lys Gln Asp Leu Lys Ala
            275             280             285
Leu Lys Glu Ala Val Lys Glu Ile Gln Thr Ser Ala Lys Ser Arg Glu
    290             295             300
Trp Asp Met Glu Ala Leu Arg Ser Thr Leu Gln Thr Met Glu Ser Asp
305             310             315             320
Ile Tyr Thr Glu Val Arg Glu Leu Val Ser Leu Lys Gln Glu Gln Gln
                325             330             335
Ala Phe Lys Glu Ala Ala Asp Thr Glu Arg Leu Ala Leu Gln Ala Leu
            340             345             350
Thr Glu Lys Leu Leu Arg Ser Glu Glu Ser Val Ser Arg Leu Pro Glu
            355             360             365
Glu Ile Arg Arg Leu Glu Glu Glu Leu Arg Gln Leu Lys Ser Asp Ser
    370             375             380
His Gly Pro Lys Glu Asp Gly Gly Phe Arg His Ser Glu Ala Phe Glu
385             390             395             400
Ala Leu Gln Gln Lys Ser Gln Gly Leu Asp Ser Arg Leu Gln His Val
                405             410             415
Glu Asp Gly Val Leu Ser Met Gln Val Ala Ser Ala Arg Gln Thr Glu
            420             425             430
Ser Leu Glu Ser Leu Leu Ser Lys Ser Gln Glu His Glu Gln Arg Leu
            435             440             445
```

```
Ala Ala Leu Gln Gly Arg Leu Glu Gly Leu Gly Ser Ser Glu Ala Asp
    450                 455             460
Gln Asp Gly Leu Ala Ser Thr Val Arg Ser Leu Gly Glu Thr Gln Leu
465                 470             475                 480
Val Leu Tyr Gly Asp Val Glu Glu Leu Lys Arg Ser Val Gly Glu Leu
            485                 490             495
Pro Ser Thr Val Glu Ser Leu Gln Lys Val Gln Glu Gln Val His Thr
            500             505             510
Leu Leu Ser Gln Asp Gln Ala Gln Ala Ala Arg Leu Pro Pro Gln Asp
        515             520             525
Phe Leu Asp Arg Leu Ser Ser Leu Asp Asn Leu Lys Ala Ser Val Ser
    530             535             540
Gln Val Glu Ala Asp Leu Lys Met Leu Arg Thr Ala Val Asp Ser Leu
545             550             555             560
Val Ala Tyr Ser Val Lys Ile Glu Thr Asn Glu Asn Asn Leu Glu Ser
            565             570             575
Ala Lys Gly Leu Leu Asp Asp Leu Arg Asn Asp Leu Asp Arg Leu Phe
        580             585             590
Val Lys Val Glu Lys Ile His Glu Lys Val
        595             600
```